(12) United States Patent
Jansson et al.

(10) Patent No.: US 12,629,636 B2
(45) Date of Patent: May 19, 2026

(54) WATER PURIFICATION APPARATUS, SYSTEM AND METHOD FOR CONTROLLING AT LEAST ONE FLUID PROPERTY

(71) Applicants: VANTIVE US HEALTHCARE LLC, Deerfield, IL (US); VANTIVE HEALTH GMBH, Glattpark (CH)

(72) Inventors: Olof Jansson, Vellinge (SE); Peter Sendelius, Staffanstorp (SE); Henrik Lindgren, Genarp (SE); Robert Hallstrom, Lund (SE); Carl-Henry Orndal, Eslov (SE)

(73) Assignees: Vantive US Healthcare LLC, Deerfield, IL (US); Vantive Health GMBH, Glattpark (CH)

(*) Notice: Subject to any disclaimer, the term of this patent is extended or adjusted under 35 U.S.C. 154(b) by 694 days.

(21) Appl. No.: 17/823,809

(22) Filed: Aug. 31, 2022

(65) Prior Publication Data

US 2022/0410068 A1 Dec. 29, 2022

Related U.S. Application Data

(63) Continuation of application No. 16/619,795, filed as application No. PCT/EP2018/065655 on Jun. 13, 2018, now Pat. No. 11,465,099.

(30) Foreign Application Priority Data

Jun. 15, 2017 (SE) .................................... 1750760-9

(51) Int. Cl.
*B01D 61/12* (2006.01)
*A61M 1/14* (2006.01)
(Continued)

(52) U.S. Cl.
CPC ............. *B01D 61/12* (2013.01); *A61M 1/155* (2022.05); *A61M 1/1561* (2022.05);
(Continued)

(58) Field of Classification Search
None
See application file for complete search history.

(56) References Cited

U.S. PATENT DOCUMENTS

2001/0010296 A1* 8/2001 Hirota ................. C02F 1/46104
210/243
2003/0173297 A1* 9/2003 Grandics ................ B01J 20/265
210/660
(Continued)

FOREIGN PATENT DOCUMENTS

AU 2006303866 2/2011
CN 1166457 12/1997
(Continued)

OTHER PUBLICATIONS

Kim et al., "The Effect of Feed Temperature on Permeate Flux During Membrane Separation," Journal of the Korean Society for Marine Environment and Energy, vol. 17, No. 1 pp. 13-19 Feb. 2014.
(Continued)

*Primary Examiner* — Richard C Gurtowski
(74) *Attorney, Agent, or Firm* — K&L Gates LLP

(57) ABSTRACT

The present disclosure relates to a water purification apparatus that comprises a reverse osmosis device, RO-device, producing a purified water flow and to a corresponding method. The proposed method comprises detecting at least one fluid property of purified water in the purified water path and regulating a flow rate of water in the recirculation path to fulfil one or more predetermined criteria of the purified water in the purified water path, based on the at least one
(Continued)

detected fluid property. The present disclosure also relates to a computer program and a computer program product implementing the method.

21 Claims, 5 Drawing Sheets

(51) Int. Cl.

| | |
|---|---|
| *A61M 1/16* | (2006.01) |
| *B01D 61/02* | (2006.01) |
| *B01D 61/48* | (2006.01) |
| *B01D 65/02* | (2006.01) |
| *C02F 1/00* | (2023.01) |
| *C02F 1/44* | (2023.01) |
| *C02F 1/469* | (2023.01) |
| *C02F 1/28* | (2023.01) |
| *C02F 101/12* | (2006.01) |
| *C02F 101/36* | (2006.01) |
| *C02F 103/02* | (2006.01) |

(52) U.S. Cl.

CPC .......... *A61M 1/1565* (2022.05); *A61M 1/159* (2022.05); *A61M 1/1686* (2013.01); *A61M 1/1688* (2014.02); *B01D 61/025* (2013.01); *B01D 61/48* (2013.01); *B01D 65/022* (2013.01); *B01D 65/027* (2013.01); *C02F 1/001* (2013.01); *C02F 1/008* (2013.01); *C02F 1/441* (2013.01); *C02F 1/4695* (2013.01); *B01D 2311/103* (2013.01); *B01D 2311/2512* (2022.08); *B01D 2311/2626* (2013.01); *B01D 2311/2649* (2013.01); *B01D 2311/2684* (2013.01); *B01D 2321/08* (2013.01); *C02F 1/283* (2013.01); *C02F 2101/12* (2013.01); *C02F 2101/36* (2013.01); *C02F 2103/026* (2013.01); *C02F 2209/02* (2013.01); *C02F 2209/03* (2013.01); *C02F 2209/40* (2013.01); *C02F 2209/44* (2013.01)

(56) References Cited

U.S. PATENT DOCUMENTS

| | | | |
|---|---|---|---|
| 2005/0139530 | A1 | 6/2005 | Heiss |
| 2007/0215546 | A1 | 9/2007 | Watkins |
| 2007/0251292 | A1* | 11/2007 | Beck ..................... G01F 1/6847 |
| | | | 73/1.35 |
| 2007/0295650 | A1 | 12/2007 | Yoneda et al. |
| 2009/0134080 | A1 | 5/2009 | Fabig |
| 2010/0229899 | A1 | 9/2010 | Andersen |
| 2011/0284377 | A1 | 11/2011 | Rohde |
| 2013/0126431 | A1 | 5/2013 | Henson |
| 2013/0302882 | A1 | 11/2013 | Nishida |
| 2014/0151297 | A1 | 6/2014 | Hulme et al. |
| 2015/0231571 | A1 | 8/2015 | Volker |
| 2025/0388494 | A1* | 12/2025 | Lieb ........................ C02F 1/441 |

FOREIGN PATENT DOCUMENTS

| | | |
|---|---|---|
| CN | 204162475 | 2/2015 |
| DE | 19520914 | 6/1996 |
| EP | 0599281 | 6/1994 |
| JP | 2000072658 | 3/2000 |
| JP | 2000126767 | 5/2000 |
| JP | 2004049977 | 2/2004 |
| JP | 2008000658 | 1/2008 |
| JP | 2009279472 | 12/2009 |
| JP | 2009279472 A | 12/2009 |
| JP | 2010-279423 | 12/2010 |
| JP | 5050996 | 10/2012 |
| JP | 2013141621 | 7/2013 |
| JP | 2014108382 | 6/2014 |
| JP | 20200518391 | 6/2020 |
| KR | 10-2007-0121541 | 12/2007 |
| WO | 2004054691 | 7/2004 |
| WO | 2016074763 | 5/2016 |

OTHER PUBLICATIONS

International Search Report; International Application No. PCT/EP2018/065655; mailed Sep. 5, 2018; 3 Pages.

Written Opinion of the International Searching Authority; International Application No. PCT/EP2018/065655; mailed Sep. 5, 2018; 6 Pages.

First Office Action and search report issued Oct. 9, 2021 from the China National Intellectual Property Administration ("CNIPA"), Chinese Application No. 2018800401874, Received: Nov. 11, 2021.

Japanese Office Action; Appln. No. 2023-219865 dated Jan. 6, 2025—13 pages.

\* cited by examiner

WATER PURIFICATION APPARATUS, SYSTEM AND METHOD FOR CONTROLLING AT LEAST ONE FLUID PROPERTY

PRIORITY CLAIM

The present application is a continuation of U.S. patent application Ser. No. 16/619,795, filed Dec. 5, 2019, now U.S. Pat. No. 11,465,099, entitled "Water Purification Apparatus And A Method For Controlling At Least One Fluid Property In A Water Purification Apparatus", which is a National Phase Entry of International Application No. PCT/EP2018/065655, filed on Jun. 13, 2018, published as WO 2018/229125 on Dec. 20, 2018, which claims priority to Swedish Application No. 1750760-9, filed on Jun. 15, 2017, the entire contents of each of which are incorporated herein by reference and relied upon.

TECHNICAL FIELD

The present disclosure relates to a water purification apparatus and to corresponding methods for controlling at least one fluid property in a water purification apparatus. The present disclosure also relates to a computer program and a computer program product implementing the method.

BACKGROUND

In treatment of patients suffering acute or chronic renal insufficiency, dialysis therapy is employed. Three general categories of dialysis therapy are hemodialysis, HD, peritoneal dialysis, PD, and continuous renal replacement therapy, CRRT.

In hemodialysis, the patient's blood is cleansed by passage through an artificial kidney in an extracorporeal membrane system, incorporated in a dialysis machine. The blood treatment involves extracorporeal circulation through an exchanger having a semipermeable membrane (dialyzer) in which the patient's blood is circulated on one side of the membrane and a dialysis fluid, comprising the main electrolytes of the blood in concentrations close to those in the blood of a healthy subject, is circulated on the other side. Furthermore, a pressure difference is created between the two compartments of the dialyzer which are delimited by the semipermeable membrane, so that a fraction of the plasma fluid passes by ultrafiltration through the membrane into the compartment containing the dialysis fluid.

CRRT is used as an alternative therapy for patients who are too ill or unstable for standard hemodialysis. It is similar to hemodialysis and makes use of a semipermeable membrane for diffusion and to some extent convection. It is however a slower form of blood treatment than hemodialysis, and may be continuously ongoing from a couple of hours up to several days.

In peritoneal dialysis, dialysis fluid is infused into the patient's peritoneal cavity. This cavity is lined by the peritoneal membrane which is highly vascularized. The metabolites are removed from the patient's blood by diffusion across the peritoneal membrane into the dialysis fluid. Excess fluid, i.e. water is also removed by osmosis induced by a hypertonic dialysis fluid. Through these two processes, diffusion and osmotic ultrafiltration, appropriate quantities of solute metabolites and fluid need to be removed to maintain the patient's body fluid volumes and composition within appropriate limits.

There are various types of peritoneal dialysis therapies, including continuous ambulatory peritoneal dialysis ("CAPD"), automated peritoneal dialysis ("APD"), including tidal flow APD, and continuous flow peritoneal dialysis ("CFPD").

CAPD is a manual dialysis treatment. The patient connects manually an implanted catheter to a drain, allowing spent dialysate fluid to drain from the peritoneal cavity. The patient then connects the catheter to a bag of fresh dialysis fluid, infusing fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from the dialysis fluid source, through the catheter, into the patient's peritoneal cavity and allow the dialysis fluid to dwell within the cavity and the transfer of waste, toxins and excess water to take place. APD machines pump spent dialysate from the peritoneal cavity, through the catheter, to the drain. As with the manual process, several drain, fill and dwell cycles occur during APD. A "last fill" occurs often at the end of CAPD and APD, which remains in the peritoneal cavity of the patient until the next treatment.

Both CAPD and APD are batch type systems that send spent dialysis fluid to a drain Tidal flow systems are modified batch systems. With tidal flow, instead of removing all the fluid from the patient over a longer period of time, a portion of the fluid is removed and replaced after smaller increments of time.

Continuous flow or CFPD systems clean or regenerate spent dialysate instead of discarding it. CFPD systems are typically more complicated than batch systems.

CAPD, APD (including tidal flow) and CFPD systems can employ a pumping cassette. The pumping cassette typically includes a flexible membrane that is moved mechanically to push and pull dialysis fluid out of and into, respectively, the cassette.

In one form of peritoneal dialysis, an automated cycler is used to infuse and drain dialysis fluid. This form of treatment may be done automatically at night while the patient sleeps. The cycler measures the amount of fluid infused and the amount removed to compute the net fluid removal. The treatment sequence usually begins with an initial drain cycle to empty the peritoneal cavity of spent dialysate. The cycler then performs a series of fill, dwell, and drain cycles, typically finishing with a fill cycle.

Peritoneal dialysis generally requires large volumes of dialysis fluid. Generally, at each application, or exchange, a given patient will infuse 2 to 3 liters of dialysis fluid into the peritoneal cavity. The dialysis fluid is allowed to dwell for approximately 1 to 3 hours, at which time it is drained out and exchanged for fresh dialysis fluid. Generally, four such exchanges are performed daily. Therefore, approximately 8 to 20 liters of dialysis fluid is required per day, 7 days a week, 365 days a year for each patient.

Dialysis fluids, for use in the above-mentioned treatments, have traditionally been provided in sealed container bag, ready for use. For example, peritoneal dialysis is typically performed using bags with three different concentration of dextrose. The bags are being delivered to a patient's home as 1 liter to 6 liter bags with different dextrose concentrations. A normal daily consumption is around 8 to 20 liters of PD dialysis fluid. The fluid is provided in sterilized bags of sizes up to six liters, which are packed into boxes and delivered, e.g., monthly, for use to the patient's home. The boxes of fluid may be cumbersome and heavy for PD patients to handle, and consume a substantial space in a room of their homes. The bags and boxes also produce a relatively large amount of waste disposed of on a weekly or monthly basis.

In light of above, several problems become apparent. Shipping and storage of the sheer volume of fluids required is space consuming. Additionally, the use of multiple pre-filled bags produces waste materials in the form of empty containers and packaging.

Sub-systems for an overall peritoneal dialysis, PD, system that creates dialysis solution at the point of use, e.g., at the PD machine are therefore needed.

PD dialysis fluid is delivered directly to the patient's peritoneal cavity. PD fluid therefore needs to have a level of sterilization suitable for being introduced into the patient's peritoneum. PD dialysis fluid is accordingly premixed and sterilized typically prior to delivery to the location of use, usually the patient's home.

Also, in hemodialysis and CRRT, systems that create dialysis solution at the point of use, e.g., at the hemodialysis machine or CRRT machine, are therefore needed.

An overall system for hemodialysis, PD or CRRT, in some embodiments, include three primary components, namely a dialysis machine, a water purifier and a disposable set operating with both the dialysis machine and the water purifier. The dialysis machine is e.g. a PD cycler, a hemodialysis machine or a CRRT machine. The dialysis machine prepares dialysis fluid from purified water from the water purifier and concentrates.

The water purifier produces purified water from e.g. tap water, at the point of use of the purified water.

SUMMARY

Under certain circumstances, it is desirable to deliver a product water flow rate of a certain size. For example, to timely be able to deliver a certain amount of purified water, or to overcome a pressure-drop caused by filters positioned downstream the water purification apparatus. However, the hardware of the water purification apparatus and filters may deteriorate over time. For example, sterilizing grade filters may be blocked by bacteria and endotoxins, and possibly other materials. This may affect the product water flow rate from the water purification apparatus. Consequently, the throughput for a constant pressure, will become less over time. Thus, the amount of purified water produced by the water purification apparatus may be uncertain. Hence, one object of the disclosure is to control properties of the product water flow to e.g. maintain a constant (or fairly constant) flow rate or pressure. Another object is to keep the working point (e.g. pressure, temperature or flow rate) of components in the water purification apparatus within certain intervals.

These objects and others are at least partly achieved by the apparatuses and methods according to the independent claims, and by the embodiments of the dependent claims.

According to a first aspect, the disclosure relates to a water purification apparatus for producing purified water. The water purification apparatus comprises a Reverse Osmosis, RO, device, a RO-pump, a recirculation path, a purified water path, a purified water path, a control device, at least one detector and a control unit. The Reverse Osmosis, RO, device is arranged to produce a purified water flow, the RO-device comprising a feed inlet arranged to receive feed water and a purified water outlet and the RO-pump is arranged to pump feed water to the feed inlet. Furthermore, the recirculation path is arranged to recirculate a proportion of the purified water flow from a first point downstream the RO-device to a second point upstream the RO-device and the purified water path is arranged to transport purified water from the purified water outlet to a product water port. The purified water path comprises a product water path arranged downstream the recirculation path to transport product water to the product water port. The control unit is configured to control the control device to regulate a flow rate of the purified water in the recirculation path, based on the fluid property detected by the at least one detector. At least one detector is arranged to detect a product fluid property of product water in the product water path. The control unit is also configured to control the control device to control a product fluid property of the product water in the product water path to fulfil one or more predetermined product water criteria, based on the product fluid property detected by the at least one detector. The at least one detector comprises a flow sensor, and the product fluid property detected by the flow sensor is a flow rate of product water in the product water path. Also, the one or more predetermined product water criteria comprises that the flow rate of product water in the product water path corresponds to a predetermined flow rate.

Hence, one or several fluid properties in the purified water path of the water purification apparatus may be controlled. More specifically, one or more product fluid properties of the product water the dialysis machine may be controlled, such that desirable product fluid properties are maintained throughout the production and also e.g. during start-up and shut-down. Here, a desired flow rate of the product water may be maintained over time.

According to some embodiments, wherein the at least one detector comprises a pressure sensor, wherein the product fluid property detected by pressure sensor is a pressure of fluid in the product water path, and wherein the one or more predetermined product water criteria comprises that the pressure of the product water in the product water path stays below a predetermined upper pressure level and/or that the pressure of the product water in the product water path corresponds to a predetermined pressure. Hence, the pressure of the product water in the product water path may be controlled to stay within a range that is desirable for optimal operation. Hence, it may be avoided that components break or become deteriorated due to a too high pressure in the product water path.

According to some embodiments, the at least one filter is arranged to filter product water flowing through the product water path and wherein the predetermined upper pressure level corresponds to a pressure tolerance level of the at least one filter or of any other component arranged in the product water path.

As water is pumped through the filters, bacteria and endotoxins, and possibly other materials may reduce the permeability of filters arranged in connection with the product water path. This means that the throughput, for a given pressure, will become less over time. By using the proposed technique, the pressure the product water in the product water path can be increased, up to the maximum allowed level, to compensate for such behavior.

According to some embodiments, the control unit is configured to activate an alarm function in response to a change of the at least one product fluid property detected by the at least one detector. Hence, the operator or patient may be warned if a suspected error is detected.

According to some embodiments, the control unit is configured to control the control device to obtain a predetermined flow rate through the product water port during a pre-determined time period, in order to produce a predetermined amount of water. Hence, an amount of product requested by the dialysis machine may be produced. The requested amount is typically between 0.5 and 400 liters, e.g. 1, 2, 5, 10, 20, 50, 70, 90, 150, 200 or 300 liters.

According to some embodiments, the water purification apparatus comprises a heater, arranged to heat the product water flowing in the product water path. Hence, product water having a temperature requested by the dialysis machine may be produced. The heater may also be used to control the temperature of a RO-membrane of the RO-device.

According to some embodiments, the water purification apparatus comprises a temperature sensor arranged to measure a temperature of water in the purified water path downstream the heater. According to these embodiments, the control unit is configured to control the control device to control the temperature of water flowing through a RO-membrane of the RO-device, based on the temperature detected by the temperature sensor. Hence, the temperature of the RO-membrane may be kept fairly constant, which may be desirable for operation.

According to some embodiments, the water purification apparatus comprises a tank arranged to receive water from an external water source and to provide water to the feed inlet.

According to some embodiments, the water purification apparatus comprises a polisher device arranged downstream the recirculation circuit in the purified water path. The polisher device for example comprises an Electro-deionization, EDI, device.

According to some embodiments, the water purification apparatus comprises a permeate water path arranged to transport purified water from the purified water outlet of the RO-device to an inlet of the polisher device.

According to some embodiments, the product water path is arranged to transport purified water from an outlet of the polisher device to the product water port.

According to a second aspect, the disclosure relates to a corresponding method for controlling at least one fluid property in a water purification apparatus producing purified water. The water purification apparatus comprises a reverse osmosis device, RO-device, producing a purified water flow, and a recirculation path arranged to recirculate a proportion of the purified water flow from a point downstream the RO-device to a point upstream the RO-device. The method comprises detecting at least one fluid property of purified water in a purified water path, including detecting at least one product fluid property of product water in a product water path of the purified water path, wherein the product water path is arranged downstream the recirculation path, and regulating a flow rate of water in the recirculation path to fulfil one or more predetermined criteria of the purified water in the purified water path, based on the at least one detected fluid property, including regulating a flow rate of water in the recirculation path to fulfil one or more predetermined product water criteria of the product water in the product water path, based on the at least one detected product fluid property. The at least one product fluid property comprises a flow rate of product water in the product water path and wherein the one or more predetermined product water criteria comprises that the flow rate of water in the product water path corresponds to a predetermined flow rate.

Hence, as described above, the product fluid properties may be controlled to fulfill certain criteria that are e.g. defined by the manufacturer or user. Thus, the production of water may be more effective and dialysis treatment may be safer. The method also enables making smaller and faster changes to the product water flow rate than when only adjusting the pumping frequency used for feeding water to the RO-device.

According to some embodiments, the method comprises estimating an amount of product water produced during a production time period based on the duration of the production time period and a corresponding flow rate of the purified water detected during the production time period. The possibility of controlling the pressure makes it possible to avoid high pressure in the product water path, which in the worst case may cause break down.

According to some embodiments, the method comprises triggering a predetermined action when the amount reaches a pre-defined production volume. For example, an alert signal or action (e.g. a message being sent to the dialysis machine) may be triggered when a requested volume has been produced.

According to some embodiments, the at least one product fluid property comprises pressure in the product water path, and wherein the one or more predetermined product water criterion comprises that the pressure of the product water in the product water path stays below a predetermined upper pressure level.

According to some embodiments, the method comprises measuring a temperature of water in the purified water path downstream a heater arranged in the purified water path. According to these embodiments the regulating then comprises regulating a flow rate of the water in the recirculation path such that the temperature of water flowing through a RO-membrane of the RO-device fulfils a predetermined temperature criterion, based on the temperature detected by the temperature sensor.

Thereby, the temperature span of the water going into the RO membrane will be less dependent on the temperature of incoming water and the ambient temperature since a returning flow of heated purified water may be used to increase the temperature of water in the tank. Consequently, the filtration behavior of the membrane will be more stable.

According to some embodiments, the method comprises continuously performing the detecting and the regulating while the water purification apparatus is producing purified water.

According to some embodiments, the method comprises activating an alarm function in response to a change of the at least one detected product fluid property. Thus, the proposed method according to these embodiments also enables the water purifier to detect sudden changes in the pressure, such as breakthrough of a filter, which means a lower pressure drop, and thereby a lower pressure and an increased flow in the product water path. Alternatively, a leakage between the water purifier and the filters will also result in a pressure drop, which should cause the alarm to go off.

According to some embodiments, the predetermined upper pressure level corresponds to a pressure tolerance level of at least one filter arranged to filter product water downstream the product water path or of any other component arranged in, or within a predetermined distance from, the product water path.

According to some embodiments, the controlling comprises controlling the fluid property of the product water to obtain a predetermined flow rate during a pre-determined time period, in order to produce a predetermined amount of water. Furthermore, the water purifier may continue to deliver the required volume to the dialysis machine even if the communication to the dialysis machine is lost. The pre-determined amount is typically between 0.5 and 400 liters.

According to some embodiments, the method comprises controlling the temperature of the product water flowing in the product water path.

According to some embodiments, a polisher device is arranged downstream the recirculation circuit in the purified water flow and then the product water path is arranged to transport product water from an outlet of the polisher device to the product water port.

According to a third aspect, the disclosure relates to a computer program comprising instructions which, when the program is executed by a computer, cause the computer to carry out the method described above and below.

According to a fourth aspect, the disclosure relates to a computer-readable medium comprising instructions, which when executed by a computer, cause the computer to carry out the method described above and below.

BRIEF DESCRIPTION OF THE DRAWINGS

Embodiments of the invention are described in more detail with reference to attached drawings illustrating examples of embodiments of the invention in which.

DETAILED DESCRIPTION

When using a water purification apparatus, for example for point of care, it might be desirable to be able to control the flow rate of the purified water i.e. product water. If the flow rate of the product water is constant, or at least known, it is possible to predict the amount of water that is produced during a certain production time.

Generally, it is desirable to produce a desired amount of product water as quickly as possible. However, if the product water flow rate is too high, the pressure of water in the water purification apparatus may be too high, which may cause damage to the fluid system and other hardware in or in connection to the water purification apparatus. Furthermore, if the product water flow rate or pressure is too high, filters in a dedicated line set arranged to provide product water e.g. to a dialysis machine might break, which may cause risk for bacteria and endotoxin to reach the patient.

The proposed technique therefore proposes a method of controlling the product water flow rate from a water purification apparatus based on one or more product fluid properties or parameters, such as a flow rate, pressure or temperature of product water in the product water path. The control is e.g. implemented using an electrically controlled proportional valve in a recirculation path of the water purification apparatus. The electrically controllable valve may also be used to control other fluid properties of the purified water, such as pressure or temperature.

For better understanding of the proposed technique a water purification apparatus, where the proposed technique may be implemented, is in the following explained as a part included in a peritoneal dialysis system. However, the proposed technique may also be implemented in a water purification apparatus that is used for producing purified water to other kinds of dialysis systems, e.g. hemodialysis or CRRT systems, for use in production of dialysis fluids to be used in the hemodialysis or CRRT treatments performed by the systems at a point of care or point of use.

Figure 1:
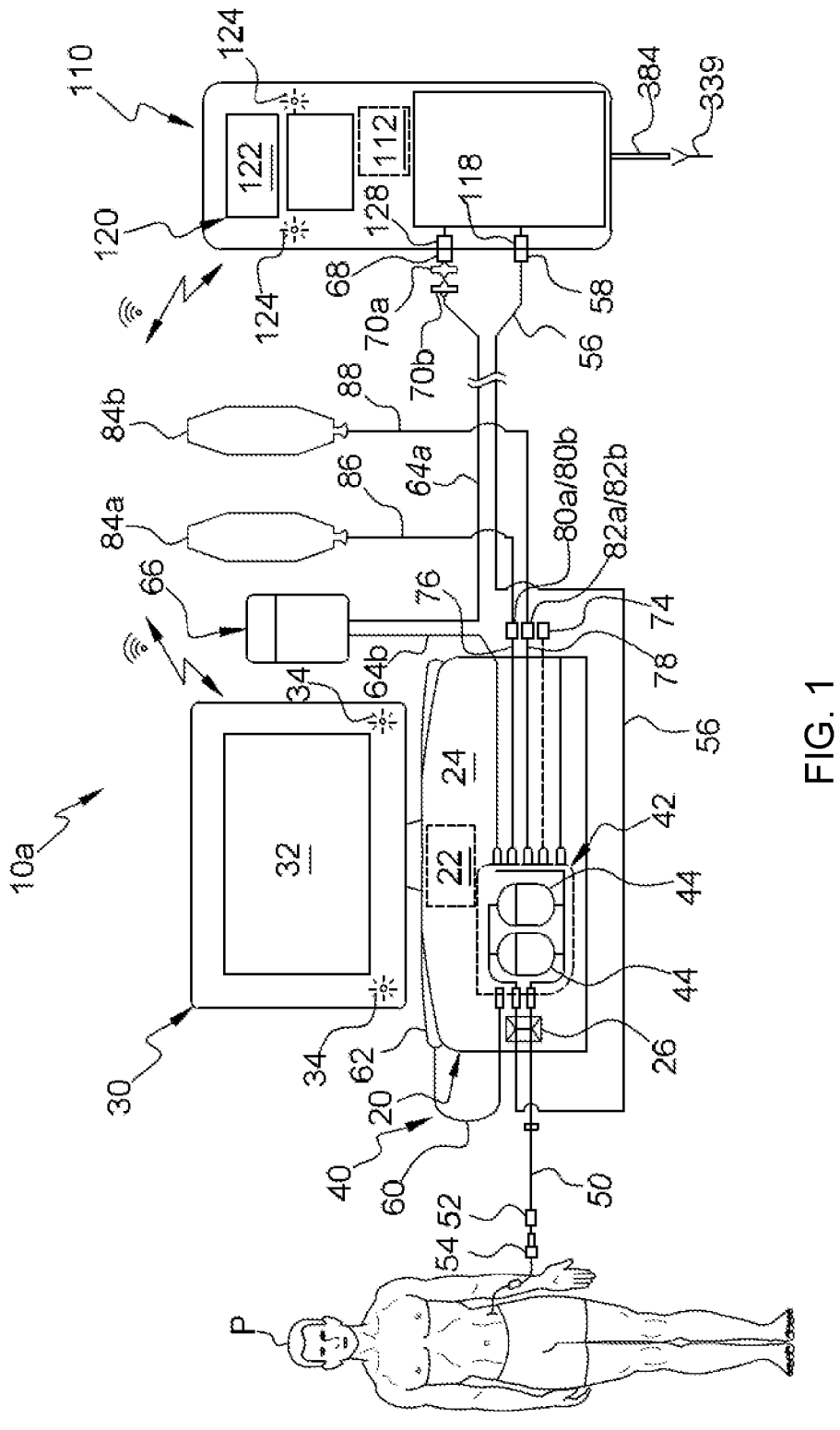
FIG. 1 is a front elevation view of one embodiment of a PD dialysis system having point of care dialysis fluid production using purified water from a water purification apparatus.

Referring now to the drawings and in particular to FIG. 1, a peritoneal dialysis system having point of use dialysis fluid production is illustrated by system 10*a*. System 10*a* includes a cycler 20 and a water purification apparatus 300. Suitable cyclers for cycler 20 include, e.g., the Amia® or HomeChoice® cycler marketed by Baxter International Inc., with the understanding that those cyclers need updated programming to perform and use the point of use dialysis fluid produced according to system 10*a*. To this end, cycler 20 includes a control unit 22 having at least one processor and at least one memory. Control unit 22 further includes a wired or wireless transceiver for sending information to and receiving information from a water purification apparatus 300. Water purification apparatus 300 also includes a control unit 112 having at least one processor and at least one memory. Control unit 112 further includes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology. The control unit 22 comprises a computer program comprising instructions which, when the program is executed by the control unit 22, cause the control unit 22 and the water purification apparatus to carry out any one or several of the methods and programs according to any one of the herein disclosed embodiments. The instructions may be saved on a computer-readable medium such as a portable memory device, e.g. a USB memory, a portable computer, or similar, and loaded into the control unit 22.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In FIG. 1, the water purification apparatus 300 includes a first drain path 384, leading to a drain 339, which can be a housing drain or drain container. The equipment programmed via control unit 22 to prepare fresh dialysis solution at the point of use may include equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, for providing positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off solenoid pneumatic valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (viii) an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in some embodiments, includes heating coils that contact a heating pan, which is located at the top of housing 24, beneath a heating lid (not seen in FIG. 1).

The cycler 20 in FIG. 1 also includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 to control unit 22. User interface 30 may also include one or more electromechanical input device, such as a membrane switch or other button.

Water purification apparatus 300 in FIG. 1 also includes a user interface 120. Control unit 112 of water purification apparatus 300 may then include a video controller, which may have its own processing and memory for interacting with primary control processing and memory of control unit 112. User interface 120 includes a video monitor 122, which may likewise operate with a touch screen overlay placed onto video monitor 122 for inputting commands into control unit 112. User interface 120 may also include one or more electromechanical input device, such as a membrane switch or other button. Control unit 112 may further include an audio controller for playing sound files, such as alarm or alert sounds, at one or more speakers 124 of water purification apparatus 300.

Figure 2:
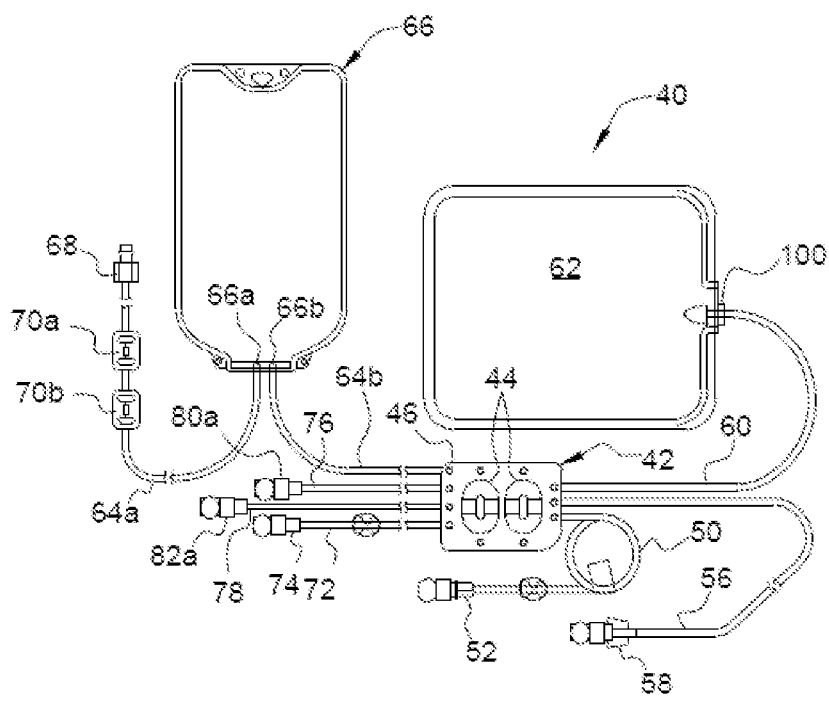
FIG. 2 is an elevation view of one embodiment of a disposable set used with the system illustrated in FIG. 1.

Referring additionally to FIG. 2, a disposable set 40 is illustrated. Disposable set 40 is also illustrated in FIG. 1, mated to cycler 20 to move fluid within the disposable set 40, e.g., to mix dialysis fluid as discussed herein. The disposable set 40 in the illustrated example include a disposable cassette 42, which may include a planar rigid plastic piece covered on one or both sides by a flexible membrane. The membrane pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

FIGS. 1 and 2 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Disposable set 40 includes a drain line 56 that extends from a drain line port of cassette 42 and terminates at a drain line connector 58. FIG. 1 illustrates that drain line connector 58 connects removably to a drain port 118 of water purification apparatus 300 to receive used dialysis fluid from the cycler 20.

FIGS. 1 and 2 further illustrate that disposable set 40 includes a heater/mixing line 60 that extends from a heater/mixing line port of cassette 42 and terminates at a heater/mixing bag 62 discussed in more detail below. Disposable set 40 includes an upstream water line segment 64a that extends to a water inlet of water accumulator 66. A downstream water line segment 64b extends from a water outlet 66b of water accumulator 66 to cassette 42. In the illustrated examples, upstream water line segment 64a begins at a water line connector 68 and is located upstream from water accumulator 66. FIG. 1 illustrates that water line connector 68 is removably connected to a product water port 128 of water purifier 110.

Water purification apparatus 300 outputs purified water and water suitable for e.g. peritoneal dialysis ("WFPD"). WFPD is water suitable for making dialysis fluid for delivery to the peritoneal cavity of patient P. WFPD is for example water for dialysis or water for injection.

In one embodiment, a sterile sterilizing grade filter 70a is placed upstream from a downstream sterile sterilizing grade filter 70b. Filters 70a and 70b may be placed in water line segment 64a upstream of water accumulator 66. Sterile sterilizing grade filters 70a and 70b may be pass-through filters that do not have a reject line. Pore sizes for sterilizing filter may, for example, be less than a micron, such as 0.1 or 0.2 micron. Suitable sterile sterilizing grade filters 70a and 70b may, for example, be Pall IV-5 or GVS Speedflow filters, or be filters provided by the assignee of the present disclosure. In alternative embodiments, only one or more than two sterile sterilizing grade filters are placed in water line segment 64a upstream of water accumulator 66. The one or several sterile sterilizing grade filters may be arranged close to the water accumulator 66, such that the disposable set 40 becomes easier to fold. In further alternative embodiments, there are no sterile sterilizing grade filters in the water line segment 64a. The sterile sterilizing grade filters may for example be replaced by one or several ultrafilters located in the product water path of the water purification apparatus 300.

FIG. 2 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 2 illustrate that disposable set 40 includes a first concentrate line 76 extending from a first concentrate port of cassette 42 and terminates at a first cassette concentrate connector 80a. A second concentrate line 78 extends from a second concentrate port of cassette 42 and terminates at a second cassette concentrate connector 82a.

FIG. 1 illustrates that a first concentrate container 84a holds a first, e.g., glucose, concentrate, which is pumped from the container 84a through a container line 86 to a first container concentrate connector 80b, which mates with first cassette concentrate connector 80*a*. A second concentrate container 84*b* holds a second, e.g., buffer, concentrate, which is pumped from container 84*b* through a container line 88 to a second container concentrate connector 82*b*, which mates with second cassette concentrate connector 82*a*.

To begin treatment, patient P typically loads cassette 42 into cycler and in a random or designated order (i) places heater/mixing bag 62 onto cycler 20, (ii) connects upstream water line segment 64*a* to product water port 128 of water purification apparatus 300, (iii) connects drain line 56 to drain port 118 of water purification apparatus 300, (iv) connects first cassette concentrate connector 80*a* to first container concentrate connector 80*b*, and (v) connects second cassette concentrate connector 82*a* to second container concentrate connector 82*b*. At this point, patient connector 52 is still capped. Once fresh dialysis fluid is prepared and verified, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

The water purification apparatus 300 will now be described in more detail.

Figure 3:
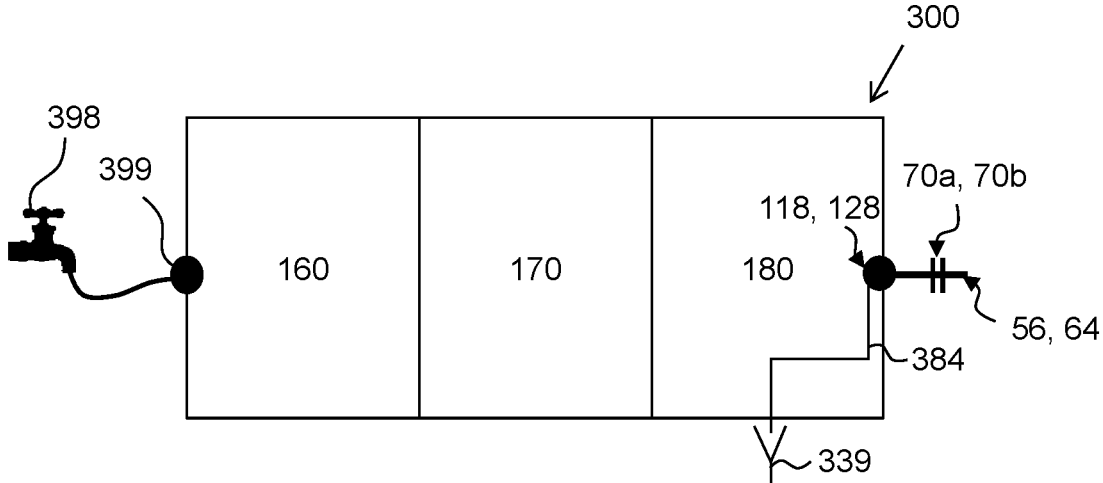
FIG. 3 is a schematic of some functional parts of the water purification apparatus.

In FIG. 3 is a schematic of the functional parts of the water purification apparatus 300, including a pre-treatment module 160, a reverse-osmosis (RO) module 170 and a post treatment module 180. The water purification apparatus 300 comprises an inlet port 399 for feeding water from a water source 398, e.g. a water tap, into the water purification apparatus 300, for purification of the water. The incoming water from the water source is fed through the inlet port 399 into the pre-treatment module 160.

Pre-Treatment Module

The Pre-treatment module 160 treats the incoming water with a particle filter and a bed of activated carbon.

The particle filter is arranged to remove particles such as clay, silt and silicon from the incoming water. The particle filter is arranged to prohibit particles in the size of micro meter, optionally also larger endotoxin molecules, from the incoming water.

The bed of activated carbon is arranged to remove chlorine and compositions with chlorine from the incoming water, and to absorb toxic substances and pesticides. In an example embodiment, the bed of activated carbon is arranged to remove one or several of hypochlorite, chloramine and chlorine. In a further example embodiment, the bed of activated carbon is also arranged to reduce organic compounds (TOC total organic carbon) including pesticides of the incoming water.

In some embodiments, the particle filter and the bed of activated carbon are integrated in one single consumable part. The consumable part is for example exchanged on a predefined interval dependent on the incoming water quality. The quality of the incoming water is for example examined and determined by qualified people before the first use of the water purification apparatus 300 at a point of care.

Optionally the pre-treatment module 160 comprises an ion exchange device for protection of downstream located devices such as a Reverse Osmosis, RO, membrane and a polisher.

The pre-treatment module 160 thus filters the incoming water and delivers pre-treated water to a downstream located RO module 170.

RO-Module

The RO-module 170 removes impurities from the filtered water, such as microorganisms, pyrogens and ionic material from the pre-treated water by the effect of reverse osmosis. The pre-treated water is pressurized by a pump and forced through RO-membrane to overcome the osmotic pressure. The RO-membrane is for example a semi-permeable membrane. Thereby the stream of pre-treated water, called feed water, is divided into a reject stream of water and a stream of permeate water. In an example embodiment, the reject water may be passed via a one or both of a first reject path and a second reject path. The first reject path recirculates reject water back to the feed water path of the RO-pump in order to be fed back into RO-device again. The recirculated reject water increases the feed flow to the RO-device, to get a sufficient flow past the reject side of the RO-membrane to minimize scaling and fouling of the RO-membrane. The second reject path directs reject water to drain. This makes the concentration level on the reject side to be sufficiently low to get an appropriate, required, permeate fluid concentration. If the feed water has low content of solutes, part of the drain flow can also be directed back to the inlet side of the RO-membrane and thereby increasing the water efficiency of the water purification apparatus 300.

The RO module 170 thus treats the pre-treated water and delivers permeate water to a downstream located post treatment module 180.

Post-Treatment Module

The post-treatment module 180 polishes the permeate water in order to further remove ions from the permeate water. The permeate water is polished using a polisher device such as an Electrodeionization, EDI, device or a mixed bed filter device.

The EDI-device makes use of electrodeionization for removing ions, from the permeate water, such as aluminum, lead, cadmium, chromium, sodium and/or potassium etc., which have penetrated the RO-membrane. The EDI-device utilizes electricity, ion exchange membranes and resin to deionize the permeate water and separate dissolved ions, i.e. impurities, from the permeate water. The EDI-device produce polished water, polished by the EDI-device to a higher purity level than the purity level of the permeate water. The EDI-device has an anti-bacterial effect of the product water and can reduce the amount of bacteria and endotoxins in the water due to, among other, the electrical field in the EDI-device. In one embodiment, the EDI-device has a capacity for producing product water of 70-210 ml/min. The capacity of the EDI-device thus sets the limit for the flow rate of the produced water.

The mixed bed filter device comprises a column, or container, with a mixed bed ion exchange material.

The polished water, herein also referred to as product water, is thereafter ready for being delivered from a product water port 128 of the water purification apparatus 300 to a point of use of the product water. The product water is suitable for dialysis, i.e. water for dialysis. In one embodiment, the product water is water for injection. In an example embodiment, a disposable set 40, including a water line 56, is arranged to the water purification apparatus 300 for transporting the product water to a point of use Optionally, the water purification apparatus 300 comprises a drain port 118. The drain port 118 is in one example embodiment used for receiving used fluid, e.g. from a PD patient, via a drain line 64, for further transport via a first drain path 384 inside the water purification apparatus 300 to a drain 339 of the water purification apparatus 300. As a further option, the drain port 118 receives a sample of ready mixed solution for further transport to a conductivity sensor arranged in the water purification apparatus 300, e.g. in the first drain path 384. The disposable set 40 is here arranged with sterilized sterile filters 70a, 70b, for filtering the product water from the water purification apparatus 300 to ensure a quality of the product water as of water for injection.

Thus, the product water collected in the accumulator bag 66 has passed through one or several sterile sterilizing grade filters of the disposable set 40 for removal of bacteria and endotoxins, i.e. to produce sterile product water. According to one embodiment, the sterile sterilizing grade filters are redundant.

By collecting the sterile product water in the accumulator bag 66, the water purification apparatus 300 and the cycler 20 are decoupled in terms of pressure, so that the high pressure needed to push water through the sterile sterilizing grade filters does not affect the cycler 20.

The control unit 112 of the water purification apparatus 300 is arranged to set the water purification apparatus 300 in different operating states, e.g. STANDBY, CONNECT, IDLE, RUN and MAINTENANCE. The water purification apparatus 300 is arranged to act upon commands from the cycler 20.

The water purification apparatus 300 is, when not in use but powered on, set in a standby state.

In STANDBY the water purification apparatus 300 waits for the command CONNECT or MAINTENANCE.

The main steps of the different states are explained. Steps done for risk mitigation, such as e.g. comparing flow sensors, testing that the flow path does not leak, and so on are omitted.

State CONNECT

During the state CONNECT the system tests sensors and checks the EDI-device to see that the system is ready when the command to go to state IDLE is received. The state CONNECT may also include flushing of certain components e.g. in the pre-treatment module 160.

The patient is typically also asked to take a sample of the incoming water, at a sampling port located after the pre-treatment module 160. What is checked in this sample is that the level of chlorine, including hypochlorite, chloramine and chlorine, are below allowed levels.

When the all steps of state CONNECT has been performed the system is ready to go.

State IDLE

In this state, the water purification apparatus 300 is waiting either for a return fluid conductivity measurement (when a newly prepared dialysis fluid is to be tested) or a new supply product water request from the cycler 20.

In this state, the water purification apparatus 300 may prepare itself for delivering product water. The water purification apparatus 300 then starts up the production of product water, but instead of delivering the product water out of the product port 128, the produced product water is recirculated to the tank 350 until the product water obtains a stable conductivity level, and the RO-device is working at a desired working point for the RO-device 301.

The water purification apparatus 300 recirculates the water path occasionally to minimize the startup time for the water production phase.

The state IDLE may also include flushing of certain components e.g. in the pre-treatment module 160.

State RUN

In state RUN the water purification apparatus 300 supplies product water (e.g. a volume requested by the cycler 20) to the disposable set accumulator bag 66.

The proposed technique will now be described in further detail referring to FIG. 4a, FIG. 4b and FIG. 5.

Figure 4A:
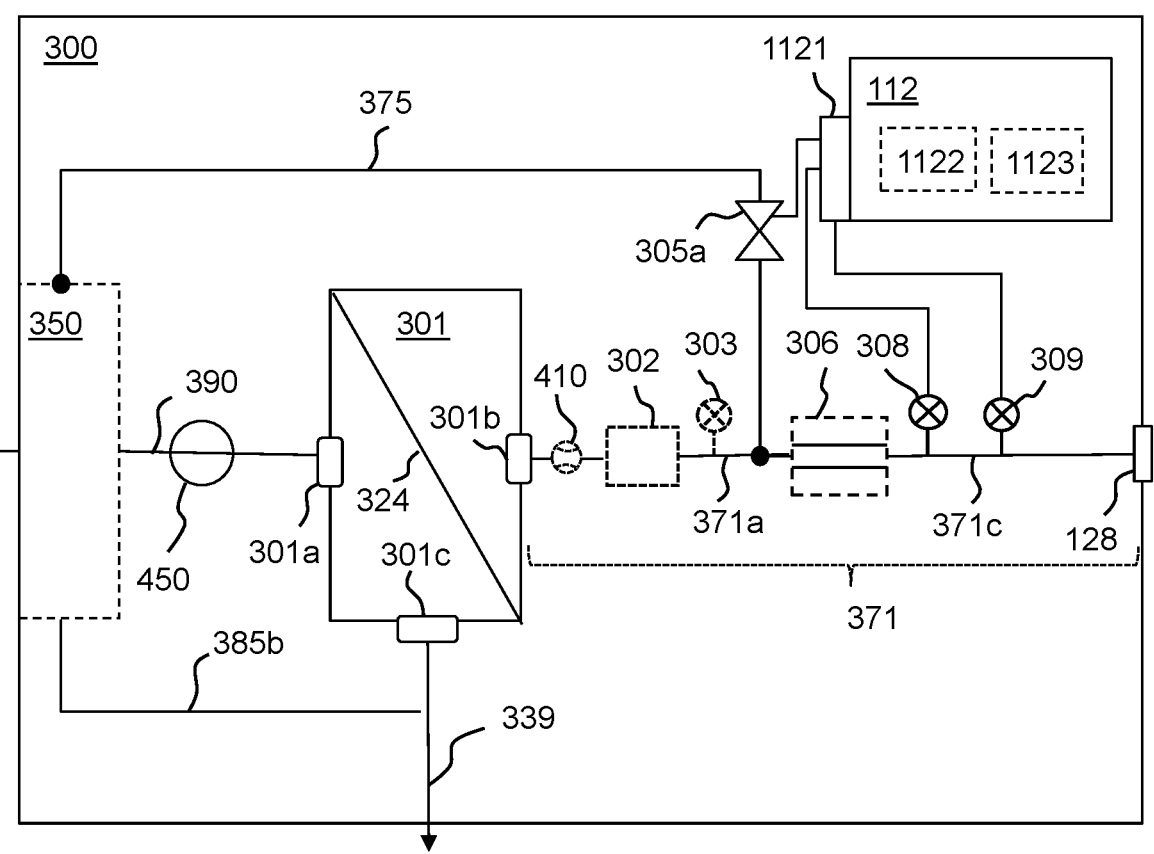
FIG. 4*a* illustrates a first exemplary embodiment of a water purification apparatus 300 comprising a RO-device 301.
Figure 5:
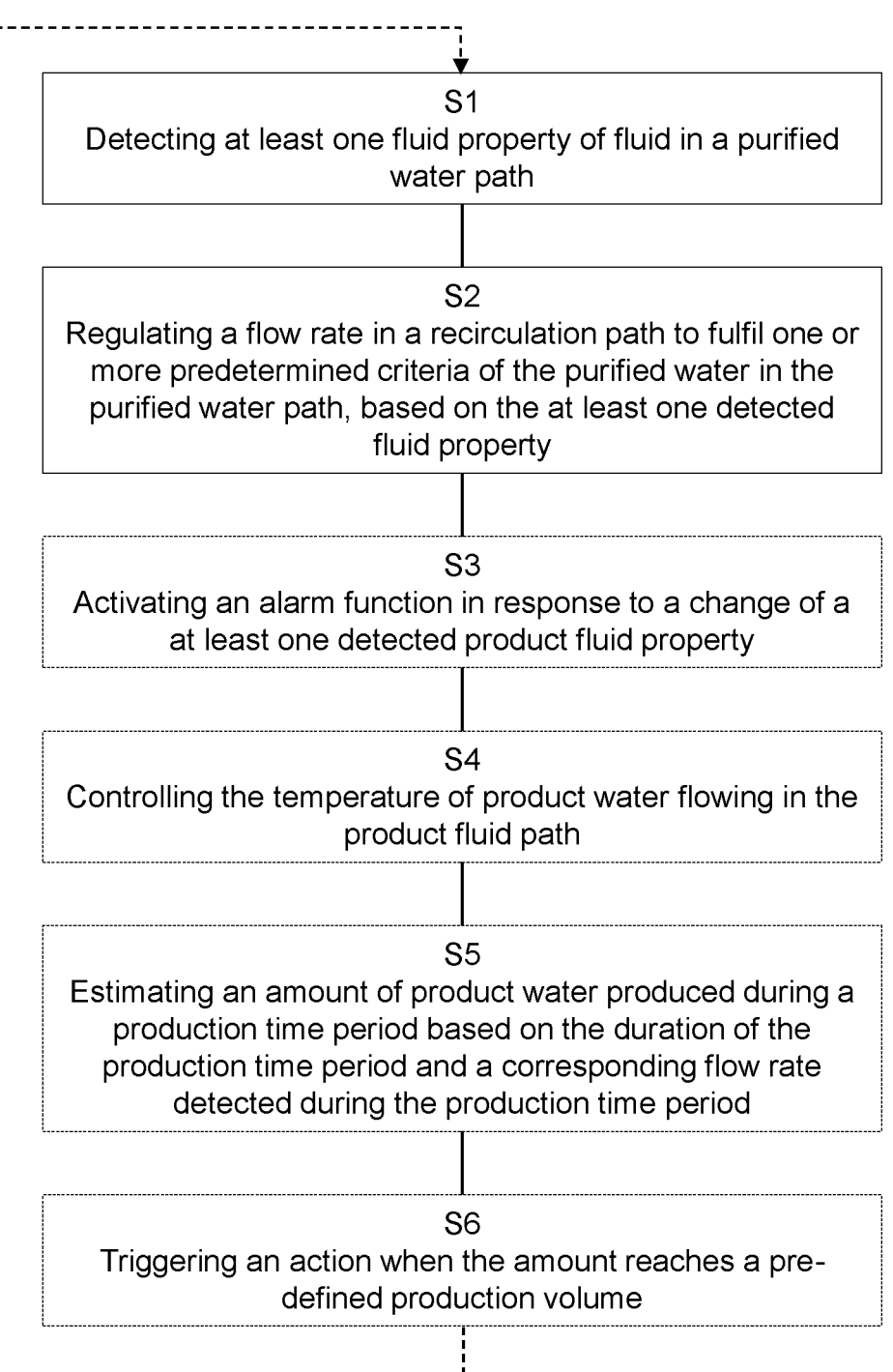
FIG. 5 illustrates a flow chart of a method for use in a dialysis machine.

FIG. 4a illustrates a water purification apparatus 300 comprising an RO-device 301. Note that FIG. 4a is only a conceptual drawing and that it only illustrates parts of the water purification apparatus 300 that are related to the proposed technique. A more detailed illustration of an exemplary water purification apparatus 300 and its operation is provided in relation to FIG. 6.

The water purification apparatus 300 of FIG. 4a comprises a RO-device 301, a tank 350, an RO-pump 450, a feed water path 390, a recirculation path 375, a purified water path 371, a control device 305a, a temperature sensor 303, a pressure sensor 308, a flow sensor 309, a heater 302, a flow sensor 380, a product water port 128 and a control unit 112.

The RO-device 301 is arranged to produce a purified water flow and a reject flow. In greater detail, the RO-device 301 comprises a RO membrane 324, a feed inlet 301a, purified water outlet 301b and a reject outlet 301c. The RO membrane 324 separates the feed inlet 301a and the reject outlet 301c, from the purified water outlet 301b. The reject flow is directed into a first reject path 385b and/or into a drain 339 of the water purification apparatus 300. The first reject path 385b is fluidly connected to the reject outlet 301c and the feed water path 390.

The feed water path 390 is arranged to transport feed water to the feed inlet 301a. The feed water path 390 is fluidly connected to the feed inlet 301a.

The tank 350 is arranged in the feed water path 390 for collecting water. More specifically, the tank 350 is arranged to receive water from an external water source and to provide water to the feed inlet 301a. According to some embodiments the tank 350 is optional, which is indicated by dashed lines in FIG. 4a.

The RO-pump 450 is arranged in the feed water path 390, to pump feed water to the feed inlet 301a. The RO-pump 450 is arranged downstream the tank 350 (when present). The RO-pump 450 is configured to be controlled to a certain pump rate corresponding to a certain flow rate of the permeate water flow. As the permeability of the RO-membrane 324 increases as the temperature of the feed water increases, the relationship between the pump rate and the flow rate is dependent on the temperature of the water fed to the feed inlet 301a, and thus the temperature of the RO-membrane 324.

The product water port 128 is arranged to provide product water e.g. to a dialysis machine, e.g. via a dedicated line set. Sterilizing grade filters (not shown) are typically located in the line set outside the water purification apparatus 300, downstream the product water port 128.

The recirculation path 375, is arranged to recirculate a proportion of the purified water flow from a first point downstream the RO-device 301 to a second point upstream the RO-device 301. More specifically, the recirculation path 375 is arranged to circulate heated purified water from a point downstream the RO-device 301, to the feed water path 390, inside the water purification apparatus 300. The purified water is in the example of FIG. 4a recirculated to the tank 350 and again fed to the feed inlet 301a of the RO-device 301. However, the purified water may alternatively be recirculated directly to the water line upstream the RO-pump 450.

The purified water path 371 is fluidly connected to the purified water outlet 301b and to the product water port 128. The purified water path 371 is configured to transport purified water from the purified water outlet 301b to the product water port 128. The purified water path 371 comprises the permeate water path 371a and a product water path 371c. The product water path herein refers to the part of the purified water path 371 closest to the product water port 128, where the fluid properties, such as pressure and flow rate, are the same (or similar) to in the product water port 128.

The heater 302 is arranged to heat the product water flowing in the product water path 371*c*. The heater 302 is e.g. a heater arranged to heat the purified water produced by the RO-device 301. Furthermore, in the example of FIG. 4*a*, purified water leaving the RO-device 301 also passes the flow sensor 410 and the temperature sensor 303 that are included in the permeate water path 371*a*.

The purified water path 371 comprises a polisher device 306, for example an ElectroDeIonization, EDI, device. Alternatively, the polisher device 306 is a mixed bed filter device. The polisher device 306 is arranged downstream the recirculation circuit 374 in the purified water path 371. Thus, the polisher device 306 is arranged in the purified water path 371 downstream the point where the recirculation path 375 is connected to the purified water path. The polisher device 306 is fluidly connected to the permeate water path 371*a* and the product water path 371*c*. In other words, according to some embodiments, the permeate water path 371*a* is arranged to transport purified water from the purified water outlet 301*b* of the RO-device 301 to an inlet of the polisher device 306 and the product water path 371*c* is arranged to transport purified water from an outlet of the polisher device 306 to the product water port 128.

This disclosure is based on the insight that a fluid property such as a pressure or flow rate of product water in the product water path 371*c*, may be controlled by controlling the portion of the permeate flow produced by the RO-device that is recirculated to the feed inlet 301*a*. The control device 305*a*, such as an electrically controllable valve, is arranged to enable such control. In other words, the control device 305*a* is arranged to regulate a flow rate of the purified water in the recirculation path 375. According to some embodiment the control device 305*a* is configured to receive control data and to regulate the proportion of the permeate flow that is recirculated based on the control data. The control data may be an electrical signal (analogue or digital). The control device 305*a* is typically a flow control device such as a proportional valve. The proportional valve is typically electrically controlled. However, a mechanical proportional valve may also be used. In one embodiment, the control device 305*a* is a pump, for example a positive displacement pump such as a volumetric pump or a piston pump.

As described above, the proposed technique enables control of at least one fluid property, such as flow rate or pressure in the product water path 371*c*, when the water purifying apparatus is operated. According to some embodiments the proposed technique enables control of other properties e.g. permeate fluid properties, such as a temperature of the RO-membrane 324 or the working point of the RO-device. To enable such control, the relevant fluid property (or properties) needs to be measured or at least somehow detected or estimated. Hence, the at least one detector is arranged to detect a fluid property of the purified water in the purified water path 371.

According to some embodiments, the at least one detector is arranged to detect a product fluid property of the product water in the product water path 371*c*. The at least one detector may be implemented in a plurality of ways. According to some embodiments the at least one detector is configured to provide product fluid property data, defining at least one product fluid property. According to some embodiments the control is based on other properties, such as permeate fluid properties, e.g. a temperature of purified water flowing in the permeate water path 371*a*.

In FIG. 4*a* the at least one detector is the flow sensor 309 and a pressure sensor 308. Then the product fluid property measured by the flow sensor 309 is a flow rate of product water in the product water path 371*c*. The product fluid property detected by pressure sensor 308 is a pressure in the product water path 371*c*. In addition, temperature sensor 303 is arranged to measure a temperature of the purified water in the permeate water path 371*a*, downstream the heater 302.

The control unit 112 typically comprises one or more microprocessors 1122 and/or one or more circuits, such as an application specific integrated circuit (ASIC), field-programmable gate arrays (FPGAs), and the like.

The control unit 112 may also comprise at least one memory 1123, such as a non-transitory memory unit (e.g., a hard drive, flash memory, optical disk, etc.) and/or volatile storage apparatuses (e.g., dynamic random access memory (DRAM)).

The control unit 112 further comprises an interface 1121 configured to enable communication with (e.g. transmit control data to and receive sensor data from) the other components of the water purification apparatus 300, and in particular with the control device 305*a* and the at least one detector, e.g. pressure sensor 308 and/or flow sensor 309.

The control unit 112 is configured to functions of the water purification apparatus 300. In particular, the control unit 112 is configured to implement all embodiments of the proposed technique described herein, including the method described in relation to FIG. 6. In order to achieve this, the control unit 112 is configured to receive fluid property data from the at least one detector and to send control data to the control device 305*a*. More specifically, the control unit 112 is configured to control the control device 305*a* to regulate a flow rate of the purified water in the recirculation path 375, based on the fluid property detected by the at least one detector e.g. to fulfil one or more predetermined criteria of the purified water in the purified water path 371. The fluid property is e.g. measured by any sensor in the purified water path 371.

According to some embodiments, the control unit 112 is configured to control the control device 305*a* to control the product fluid property of the product water in the product water path 371*c* to fulfill one or more predetermined product water criteria, based on the fluid property detected by the at least one detector, e.g. pressure sensor 308 and/or flow sensor 309. In other words, the control unit 112 is configured to control the flow rate of water in the recirculation path 375 in order to fulfil one or more criteria, such as obtaining certain fluid properties, e.g. a certain pressure or flow rate, in the product water flow.

As explained above, different product fluid properties may be controlled. Thus, the product water criteria may comprise one or more regulation conditions. Some examples will now be given. It must be understood that those could be used singly or in combination. In the simplest form, the at least one product water criteria only comprise one single condition.

In a first example, the goal of the control is to achieve a constant product water flow rate. The control criteria would then be to attempt to keep a constant product water flow rate through the product water port 128. The flow rate through the product water port 128 is typically the same (or at least about the same) as in the entire product water path 371*c*. Thus, according to some embodiments the predetermined criteria comprises that the flow rate of product water in the product water path 371*c* corresponds to a predetermined flow rate, e.g. 150 ml/min or 250 ml/min. If a constant flow rate of product water may be obtained it is easy to estimate how long time it will take to produce a certain amount of product water.

For example, the water purification apparatus 300 may be controlled to produce product water with a certain constant product water flow during a predetermined time period. In other words, according to some embodiments the control circuitry is configured to control the control device 305*a* to obtain a predetermined flow rate through the product water port 128 during a pre-determined time period, in order to produce a predetermined amount of water. The pre-determined amount is for example between 0.5 and 400 liters. The pre-determined amount may correspond to the amount needed for one or several dialysis treatments. For example, the water purification apparatus 300 may be controlled to produce 0.5, 1, 2, 5, 10, 20, 50, 70, 90, 150, 200, 250, 300 or 400 liters of purified water.

In a second example, the goal of the control is to achieve a limited or controlled product water pressure. The pressure of the product water in the product water path 371*c* should typically not exceed a maximum allowed level. The maximum allowed level would e.g. be to ensure that hardware, such as filters inside or in connection with the water purification apparatus or the polisher device 306, are not damaged. In other words, according to some embodiments, the predetermined upper pressure level corresponds to a pressure tolerance level of the at least one filter (e.g. the sterilizing grade filters) or of any other component arranged in the product water path 371*c*. Thus, according to some embodiments the predetermined criteria comprises that the pressure of the product water in the product water path 371*c* stays below a predetermined upper pressure level.

A typical implementation of the predetermined criteria could e.g. comprise controlling the control device 305*a* to attempt to obtain a predetermined flow rate of product water in the product water path 371*c* as long as the pressure of the product water in the product water path 371*c* remains below a predetermined upper pressure level. If the pressure reaches the predetermined upper pressure level then the control device 305*a* will instead control the control device to keep the pressure at that level, even if the flow rate of product water in the product water path goes below the predetermined flow rate.

As discussed above the throughput, for a given product water pressure, will become less over time. By controlling how much of the permeate is recirculated in the recirculation path 375, the product water pressure can be successively increased, to compensate for such behavior. In other words, according to some embodiments the predetermined product water criteria comprises that the pressure of the product water in the product water path 371*c* corresponds to a pressure level. The pressure level in the product water path 371*c* may e.g. correspond to an expected throughput through the product water port 128 and may thus vary (typically increase) over time.

In a third example the goal of the control is to maintain a certain working point of one or more of the hardware components of the water purification apparatus 300, such as a hardware component in the permeate water path 371*a* or the polisher water path 371*b* (FIG. 6), e.g. the RO-device 301 (which is considered to at least partly be included in the permeate water path 371*a*) or the polisher device 306. The working point is e.g. a certain pressure, a certain flow rate or a certain temperature. A working point criterion is then typically formulated to keep the working point within a certain interval.

For example, the flow rate or pressure of water in the permeate water path 371*a* directly downstream the RO-device 306 is measured (or estimated) using flow sensor 410. In principle, any detector in the permeate water path 371*a* or the polisher water path 371*b* may be used.

Then a permeate fluid property, such as a pressure in the RO-device (in particular a trans-membrane pressure of the RO-membrane) or a flow rate through the polisher device 306, may be controlled using the control device 305*a*.

In other words, according to some embodiments the control unit 112 is configured to control the control device 305*a* to control a permeate fluid property (e.g. to fulfil a working point criterion of the RO-membrane 324 or polisher device 306) of the permeate water in the permeate water path 371*a* to fulfil one or more predetermined permeate water criteria, based on the permeate fluid property detected by the at least one detector e.g. temperature sensor 302 or flow sensor 410.

In a fourth example the goal is to keep the working temperature of the RO-membrane 324 of the water purification apparatus 300 at a constant temperature, independently on e.g. the temperature of inlet water fed through the inlet port 399 (FIG. 3) or the temperature of the surroundings. Constant temperature is generally desirable, as the working properties, such as throughput and purification properties, of the RO-membrane 324 are typically dependent on the temperature of the RO-membrane 324. A constant working temperature of the RO-membrane may be achieved by keeping the temperature of the water going through the RO-membrane 324 constant. The temperature T_RO of water going through the RO-membrane 324 is (at least basically) the same as the temperature of the purified water in the permeate water path 371*a* directly downstream the RO device 301, i.e. upstream the heater 302. This temperature depends on several factors such as the temperature of inlet water fed to the inlet port 399 (FIG. 3), the proportion of heated water being recirculated in the recirculation path 375 and the temperature of the recirculated water, i.e. the temperature T2 of the purified water after the heater.

The relation of the temperature T_RO of purified water before the heater 302 and the temperature T2 of purified water after the heater 302 may be calculated using thermodynamics and the formula:

$$P = Q \times cp \times \Delta T \rightarrow T\_RO = T2 - P/(Q \times cp) \qquad \text{(Equation 1)}$$

In the formula P is the power (Watt) of the heater 302, Q is the flow rate through the heater 302 [l/s] (which is the same as the flow rate through the RO-membrane 324), T2 is the temperature of the purified water downstream the heater 302 and T_RO is the temperature upstream the heater 302 (i.e. the temperature of the water flowing through the RO-membrane 324). Thus, $\Delta T$ is the temperature difference between the water upstream the heater 302 and the water downstream the heater 302, i.e. $\Delta T = T2 - T\_RO$. Furthermore cp is the heat capacity of water. Heat capacity or thermal capacity is a measurable physical quantity equal to the ratio of the heat added to (or removed from) an object to the resulting temperature change. The heat capacity of water is 4.19 kJ/K. For example, if the flow rate Q through the RO-membrane 324 is 210 ml/min (i.e. 0.0035 l/s) and the temperature of the purified water in the permeate water path T2 is 85° C. and the heating power P is 200 W then the resulting temperature of the RO-membrane would be estimated to:

$$T_{RO} = 85 - 200/(0.0035 \times 4190) = 85 - 13.6° \text{ C.} = 71.4° \text{ C.} \qquad \text{(Equation 2)}$$

The temperature T2 of the purified water in the permeate water path 371a may be measured using temperature sensor 303. Thus, the temperature of the RO-membrane 324, or rather the temperature of the water flowing through the RO-membrane 324, may be estimated from the measured temperature T2 of the purified water in the permeate water path, as the power of the heater 302 and the flow rate Q through the RO-membrane 324 are known.

For example, if a change in the temperature T2 of the purified water in the permeate water path 371a is detected, while the power of the heater 302 and the flow rate Q through the heater are kept constant, it is an indication that the temperature T_RO of feed water going through the RO-membrane 324 has changed due to e.g. a change in temperature of the inlet water or of the surroundings.

One way of achieving the goal of keeping T_RO constant, is then to adjust the power P supplied by the heater (i.e. to control the temperature of the recirculated water) or to change flow rate Q through the heater 302 in response to a measured change of the temperature T2 of the purified water in the permeate water path 371a. The flow rate Q of water flowing through the heater 302 (and the RO membrane 324) may be controlled by changing the pumping frequency of the RO-pump 450. However, it is in some embodiments desirable to use one single pump frequency for every batch of water.

Another way of achieving the goal of keeping T_RO constant, is to change the amount of heated water that is recirculated in the recirculation path 375. For example, if more heated water is recirculated, then the temperature of the water in the tank 350 will increase. This would in turn increase the temperature of the feed water fed though the feed inlet 301a and consequently also of the temperature T_RO of water going through the RO-membrane 324.

From above follows that the temperature T_RO of water going through the RO-membrane 324 may be estimated from the measured temperature T2 of the purified water in the permeate water path 371a, using Equation 1. The temperature T_RO of water going through the RO-membrane 324 may then be kept constant, by controlling the control device 305a to regulate the proportion of the permeate flow recirculated in the recirculation path, based on the estimation. For example, the proportion of the permeate flow recirculated in the recirculation path may be continuously adjusted such that the estimated temperature T_RO of water going through the RO-membrane 324 is kept constant.

In other words, according to some embodiments, the control unit 112 is configured to control the control device 305a to control the temperature T_RO of water flowing through the RO-membrane 324, based on the temperature detected by the temperature sensor 303. Typically, the control unit 112 is configured to control the control device 305a to control the temperature T_RO such that a predefined temperature criterion is fulfilled. The criterion e.g. comprises that the temperature T_RO of water flowing through the RO-membrane 324 is kept within a predefined interval.

Thus, the control device 305a may be controlled to keep the temperature of the water after RO-membrane 324 at a predetermined temperature or within a predetermined temperature interval.

The third and the fourth examples may be used in combination with the embodiments above, and corresponding product water criteria, that are intended to control a product fluid property of product water in the product water path 371c. Then the different criteria relating to pressure, flow and temperature then need to be combined (e.g. prioritized and weighted) for optimal control.

In an alternative embodiment, these (third and fourth) embodiments are independent on the embodiments described above. Then the control unit 112 may then not be configured to (at least not at the same time) control the control device 305a to control the product fluid property of the product water in the product water path 371c to fulfil one or more predetermined product water criteria, but instead to only e.g. control the control device 305a to control the temperature of water flowing through the RO membrane 324, based on the temperature detected by the temperature sensor 303.

According to some embodiments, the control unit is configured to activate an alarm function in response to a change of the at least one product fluid property detected by the at least one detector, e.g. pressure sensor 308 and/or flow sensor 309. For example, in order to minimize the risk that the predetermined upper pressure level is exceeded the control unit 112 may be configured to trigger an alarm if the pressure measured by the pressure sensor exceeds the predetermined upper pressure level.

The alarm may alternatively be triggered in response to a significant or sudden pressure decrease or similar, which would serve as an indication of a failure. For example, a breakthrough in a filter, such as the sterilizing grade filters may result in a pressure drop, and thereby in a decreased pressure and increased flow rate of product water in the product water path 371c. As those events do not match the control unit 112 may issue an alarm in such a situation.

In another example, a leakage out of the system between the water purification apparatus 300 and the sterilizing grade filters 70a, 70b will also result in a drop of the pressure of the product water in the product water path 371c. A leakage would also be a severe error that should trigger an alarm.

In other words, according to some embodiments the control unit 112 is configured to activate an alarm function in response to a pressure change measured by the pressure sensor 308 and/or a flow rate change measured by the flow sensor 309.

Figure 4B:
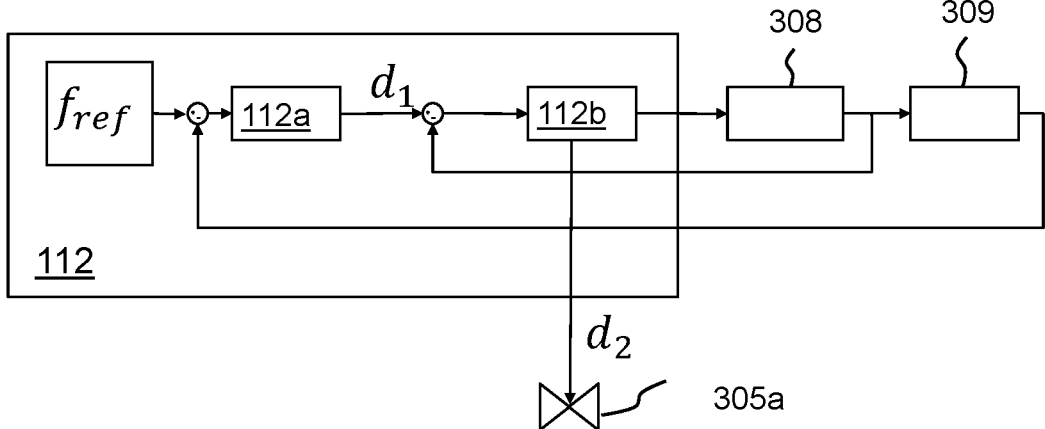
FIG. 4*b* illustrates the functionality of a control unit of the water purification apparatus 300.

FIG. 4b illustrates the functionality of the control unit 112 of the water purification apparatus 300 according to one example implementation. In this example, control unit comprises a cascade control arrangement, comprising flow rate controller 112a and a pressure controller 112b. In a cascade control arrangement, there are two (or more) controllers of which one controller's output drives the set point of another controller.

In this example, the flow rate controller 112a is driving the set point of the pressure controller 112b to obtain a pre-determined flow rate of product water in the product water path 371c. In other words, the flow rate controller 112a, generates first control data to the pressure controller 112b $d_1$ based on the flow rate of product water in the product water path 371c measured by the flow sensor 309 and a reference flow rate $f_{ref}$, e.g. 200 ml/min.

The pressure controller 112b, in turn, drives the control device 305a to match the flow rate with the set point the flow rate controller 112a is requesting, as long as the pressure does not exceed a preset pressure level, e.g. 300 kPa. In other words, the pressure controller 112b, generates second control data $d_2$ based on the pressure of the product water in the product water path 301c measured by the pressure sensor 308 and the first control data $d_1$. The pressure controller 112b then controls the control device 305a using the second control data $d_2$.

The controller driving the set point (the flow rate controller 112a in the example above) is called the primary, outer, or master controller. The controller receiving the set point (pressure controller 112*b* in the example) is called the secondary, inner or slave controller. The control loop frequency of the inner loop may typically be higher than the outer loop. For example, the control loop frequency of the pressure controller 112*b* is 10 Hz.

A corresponding method for controlling at least one fluid property in a water purification apparatus 300 producing purified water will now be described, with reference to the flow chart of FIG. 5, and the exemplary embodiments of the other figures.

The method is typically performed in the control unit 112 of the water purification apparatus 300. The method may be implemented as program code and saved in the memory 1123 in the control unit 112. Thus, the steps of the method may be defined in a computer program, comprising instructions which, when the program is executed by a computer e.g. the control unit 112, cause the computer to carry out the method. Thus, the steps of the method may also be defined in a computer-readable medium, e.g. a removable memory such as a USB memory stick. The computer-readable medium then comprises instructions, which, when executed by a computer, cause the computer to carry out the method.

In a typical scenario, the method is performed when the water purification apparatus is in state RUN and the purification apparatus supplies the product water to e.g. a dialysis machine. However, it must be appreciated that the proposed method may also be performed in the state CONNECT or IDLE, when no product water is delivered, but instead recirculated in the additional recirculation path 381 as described in FIG. 6.

The method comprises detecting S1 at least one fluid property of purified water in a purified water path 371.

According to some embodiments the detecting S1 comprises detecting at least one product fluid property of a product water in a product water path 371*c* of the purified water path 371. As described above (FIG. 4*a*) the product water path 371*c* is arranged downstream the recirculation path 375. This step implies that the product fluid properties, such as pressure and flow rate of product water in the product water path, are measured. Typically, the corresponding sensors 308, 309 produce sensor data that is provided to the control unit 112 performing the method.

The method further comprises regulating S2 a flow rate of water in the recirculation path 375 to fulfil one or more predetermined criteria of the purified water in the purified water path 371, based on the at least one detected fluid property.

According to some embodiments the regulating S2 comprises regulating a flow rate of water in the recirculation path 375 to fulfil one or more predetermined product water criteria of the product water in the product water path 371*c*, based on the at least one detected product fluid property. Stated differently, the flow rate of water in the recirculation path 375 is adjusted, in order to control certain product fluid properties.

Alternatively, the regulating S2 comprises regulating a flow rate of water in the recirculation path 375 to fulfil one or more predetermined permeate water criteria of the permeate water in the permeate water path 371*a*, based on the at least one detected product fluid property. One example of a permeate water criteria is that the permeate water has a certain pressure or temperature.

For example, the flow rate of water in the recirculation path 375 is adjusted such that the flow rate of product water in the product water path 371*c* is constant or within a predetermined interval. In other words, according to some embodiments, the at least one product fluid property comprises a flow rate of product water in the product water path 371*c* and then the predetermined product water criterion comprise that the flow rate of product water in the product water path 371*c* corresponds to a predetermined flow rate.

In another example, the flow rate of water in the recirculation path 375 is adjusted such that the pressure of the product water in the product water path 371*c* does not exceed a threshold. In other words, according to some embodiments, the at least one product fluid property comprises the pressure of the product water in the product water path 371*c*. Then the predetermined product water criteria comprise that the pressure of the product water in the product water path 371*c* stays below a predetermined upper pressure level.

The detecting S1 and the regulating S2 are typically continuously performed in the state RUN. Hence, every change detected by the at least one detector, e.g. pressure sensor 308 and flow sensor 309, may trigger the regulation S2. Stated differently, the method comprises comprising continuously performing the detecting S1 and the regulating S2 while the water purification apparatus 300 is producing purified water. The predetermined upper pressure level for example corresponds to a pressure tolerance level of at least one filter arranged to filter product water flowing through the product water path 371*c* or of any other component arranged in, or within a predetermined distance from, the product water path 371*c*.

According to some embodiments, the method comprises activating S3 an alarm function in response to a change of the at least one product fluid property. In other words, if the detecting reveals a certain change e.g. a sudden pressure-increase or decrease, this might be considered an indication of a potential error, as exemplified above in relation to FIG. 4*a*. In such situation, an alarm function that alerts the user about the potential error might be triggered. The alarm might be a sound, a flashing light or a text message sent or displayed to the user.

In some situations, it might be desirable to produce product water having a certain temperature. The temperature is e.g. requested by the dialysis machine to which the water purification apparatus 300 is requested to deliver purified water to. The temperature of the product water may then be controlled accordingly. Hence, according to some embodiments, the method comprises controlling S4 the temperature of product water flowing in the product water path 371*c*. This might be done by heating, by means of the heater 302. The temperature can be set to virtually anything, but the range may be limited to 20 to 35° C.

If the flow rate of the product water is continuously detected, then it is also possible to calculate how much water has passed through the product water path 371*c*, as the amount would correspond to the integral of the flow rate. According to some embodiments, the controlling comprises estimating S5 an amount of product water produced during a production time period based on the duration of the production time period and a corresponding flow rate of the purified water detected during the production time period. The production time period would typically correspond to a time from when the production started until it ended, or until a current time, if production is ongoing, i.e. production has not ended.

In the second scenario, i.e. when the production is ongoing, a predetermined action, such as an alarm or notice, may be triggered when a desired amount of product water has been produced. The desired amount may e.g. be specified by the user and input via the user interface. In other words, according to some embodiments, the method comprises triggering S6 a predetermined action when the amount reaches a certain production volume. The action might be that the production is halted, that an attached dialysis machine is informed or that an alarm is triggered.

According to some embodiments, the controlling comprises controlling the fluid property of the purified water through the product water port 128 to obtain a predetermined flow rate during a pre-determined time period, in order to produce a predetermined amount of water. The pre-determined amount is for example between 0.5 and 400 liters. The pre-determined amount may e.g. correspond to the volume required for one dialysis treatment, or to several treatments.

As described above, it may also be desirable to keep the working temperature of the RO-membrane 324 fairly constant. Hence, according to some embodiments the method comprises measuring a temperature of water in the purified water path 371 downstream a heater 302 arranged in the purified water path. Then the regulating S2 comprises regulating a flow rate of water in the recirculation path such that the temperature T_RO of water flowing through the RO-membrane 324 fulfils a predetermined temperature criterion, based on the temperature detected by the temperature sensor 303. As discussed above the regulating may in some embodiments be performed in this way in combination with or independently on the other embodiments described herein.

Figure 6:
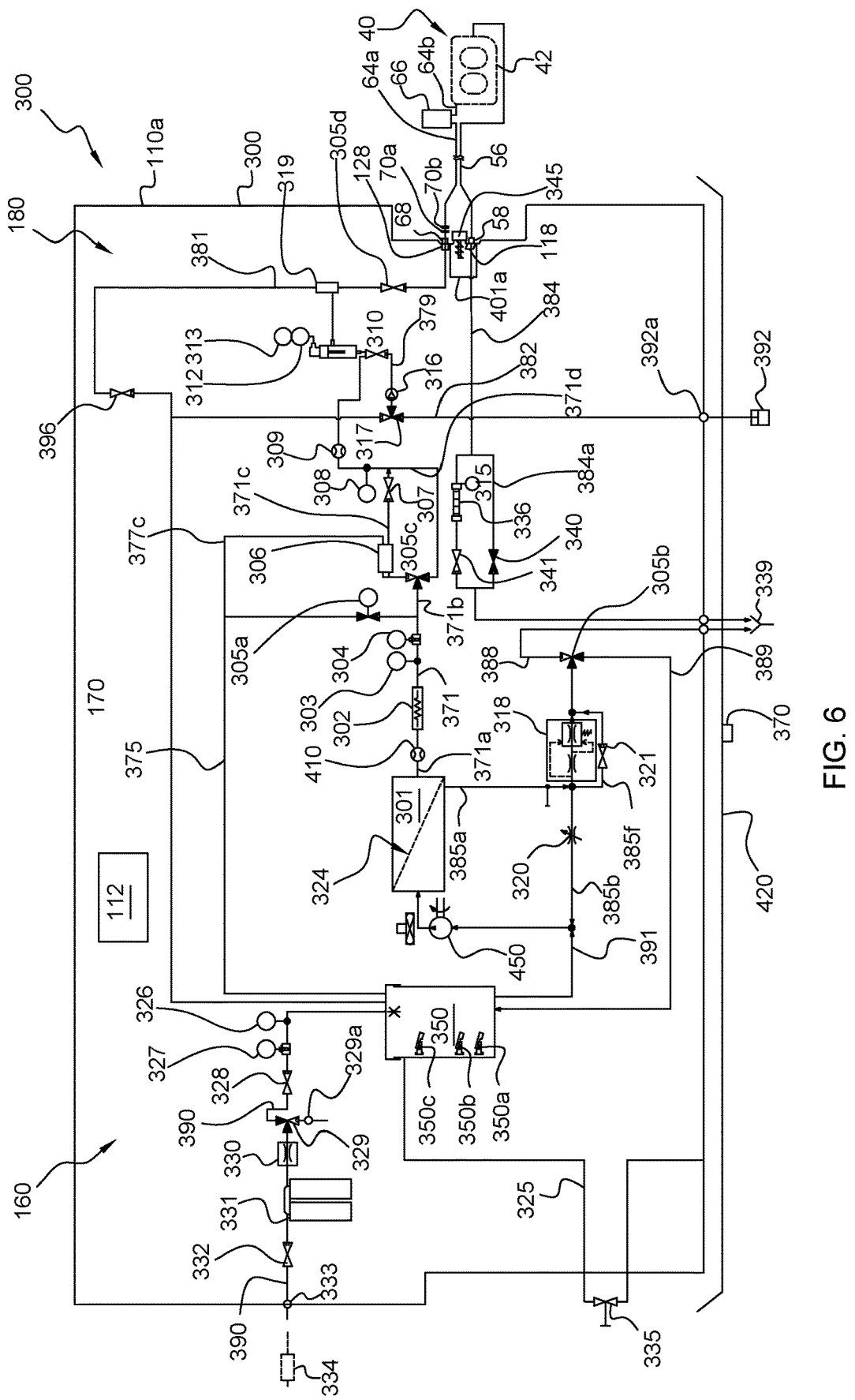
FIG. 6 illustrates an example water purification apparatus in greater detail.

FIG. 6 illustrates an example implementation of the water purification apparatus 300 according to some embodiments in more detail. In other embodiments, the water purification apparatus 300 may include less or more components or modules.

The water purification apparatus 300 of FIG. 6 receives water from a water source 398 (FIG. 3), such as a continuous source of potable or drinkable water from a patient's home. In various embodiments, water purification apparatus 300 may be installed in a room having access to the water source 398 to provide WFPD to cycler 20 as discussed herein. The water is optionally filtered using a particle pre-filter 334 to remove dirt and sediment, before it is delivered to the water purification apparatus 300. The water enters the water purification apparatus 300 via the water inlet port 333. As previously described, the water purification apparatus 300 includes a pre-treatment module 160, a RO-module 170 and a post-treatment module 180. The pre-treatment module 160 includes a particle filter and an activated carbon filter, i.e. an activated carbon bed, to further remove contaminants and impurities. The particle filter and the activated carbon filter are embodied in filter package 331. The filter package 331 is a disposable package. The pre-treatment module 160 includes an inlet valve 332 and a constant flow device 330 upstream the filter package 331. The inlet valve 332 controls the feed water inflow under control of control unit 112. The constant flow device 330 provides a constant flow to the tank 350 providing that the water pressure is above a minimum pressure for inlet valve 332.

Furthermore, pre-treatment module 160 comprises a sampling valve 329 with a sampling port outlet 329a, a tank valve 328, a pre-treatment conductivity sensor 327 and a feed water temperature sensor 326 downstream the filter package 331. The sampling port outlet 329a allows a sample to be taken from the feed water, e.g. to test the chlorine level. The tank valve 328 controls the flow of filtered feed water to the tank 350. The pre-treatment conductivity sensor 327 monitors the conductivity of the filtered feed water, and the feed water temperature sensor 326 monitors the temperature of the filtered feed water. The temperature of the filtered feed water is for example needed to calibrate the conductivity measurement of the filtered feed water. The described components are included in the feed water path 390. The feed water path 390 is connected to the water inflow port 333 and ends into the tank 350. The inlet valve 332 and the tank valve 328 are configured to be controlled by control unit 112 of the water purification apparatus 300. Water softening in the pre-treatment module 160 may alternatively or additionally be achieved using lime softening, ion-exchange resins or an anti-scalant such as polyphosphate, as known in the art. It should be appreciated that the filter package 331 is in some embodiments not required and may not be present.

As explained above, the RO-module 170 comprises a tank 350, a RO-pump 450 and a RO-device 301. A RO-device 301 has already been described in detail with reference to the FIG. 4a and reference is made to that description for further explanation. The filtered (or unfiltered) feed water enters the tank 350, for example from an upper part of the tank 350. Feed water is accumulated in the tank 350 and pumped by the RO-pump 450 to the feed inlet 301a (see FIGS. 5-7) of the RO-device 301.

Empty, low and high-level switches 350a, 350b, 350c are provided in tank 350 detect its water level, while a computer program run on control unit 112 of water purification apparatus 300 is configured to control the opening and closing of inlet valve 332 and tank valve 328, which are open during the filling of tank 350, and closed when the water level in tank 350 activates its high-level switch 350c connected to control unit 112. Inlet valve 332 opens again when the water level falls below low-level switch 350b of tank 350, thus tripping the low-level switch connected to control unit 112. If the water level in the tank 350 rises too high, excess water is drained via a tank air vent line 325 and tank air vent 335 (overflow connection), e.g. to a tray 420 or drain 339. The tank air vent 335 is accessible from outside the water purification apparatus 300. The tank air vent 335 may be closed e.g. during transport of the water purification apparatus 300, such that any water in the tank 350 will be prevented to flow to the tray 420 and cause water to flow out of the water purification apparatus 300.

The control unit 112 is configured to cause the RO-pump 450 to stop pumping, if empty level switch 350a in tank 350 detects air or a critically low water level. RO-pump 450 is configured to provide the water flow and pressure requisite for the reverse osmosis process taking place at RO-device 301. As previously described e.g. with reference to FIG. 4a, the RO-device 301 filters water to provide purified water at its permeate water outlet. 301b. Reject water leaving RO-device 301 at a reject outlet 301c (may be fed back into RO-pump 450 to conserve water consumption or alternatively be pumped to drain 339.

Purified water leaving the RO-device 301 is transported in a purified water path 371 inside the water purification apparatus 300 before being output through a product water port 128. The purified water path 371 comprises (as in FIG. 4a) permeate water path 371a, polisher water path 371b and product water path 371c. The polisher device 306 may be by-passed passed via the by-pass path 371d. The by-pass path 371d is connected to the water path upstream the polisher device 306, here an EDI-device, and to the water path downstream the EDI-device. Purified water leaving the RO-device 301 passes a flow sensor 410, a heater 302, and a permeate temperature sensor 303, included in the permeate water path 371a. The flow sensor 410 monitors the flow of the purified water leaving the RO-device 301. The heater 302, heats, under control of the control unit 112, the purified water leaving the RO-device 301. The permeate temperature sensor 303 monitors the temperature of the purified water leaving the RO-device 301 directly downstream the heater 302. An additional conductivity sensor 304 monitors the conductivity of purified water leaving RO-device 301.

Downstream the heater 302, the permeate temperature sensor 303 and the conductivity sensor 304, the purified water enters the post-treatment module 180 via the polisher water path 371*b*. The post-treatment module 180 comprises the polisher device 306. The three-way valve 305*c* is arranged to be controlled by the control unit 112 to selectively direct the purified water flow into either the polisher device 306, or into the bypass path 371*d* in order to bypass the polisher device 306. The polisher device 306 device is configured to produce product water. A product channel valve 307 regulates the flow rate of the product water in the product water path 371*c* from the polisher device 306. The concentrate water path 377*c* is arranged to pass fluid from the polisher device 306 back to the tank 350.

The product water is passed to the product water port 128, and further into a thereto connected water line 64 (64*a*, 64*b*) of the disposable set 40 for transport to the point of care. The disposable set 40 comprises two sterile sterilization filters 70*a*, 70*b*. The sterile sterilization filters 70*a*, 70*b* filter the product water leaving the product water port outlet 128 into sterilized product water, that is suitable for injection. According to some alternative embodiments those filters are left out or the number of filters is less or more than two.

A drain port 118 defines a first drain path 384 to the drain 339. A drain line 56 of the disposable set 40 is connected to the drain port 118, in order to pass water, such as used PD-fluid, from the drain port 118 to the drain 339. The first drain path 384 here embodies the part of a cycler drain path that is present inside the water purification apparatus 300. The first drain path 384 comprises a conductivity sensor 336, a drain path temperature sensor 315 and a drain line valve 341. The conductivity sensor 336 is configured to measure the conductivity of the water in the drain path. The temperature sensor 315 is arranged to measure the temperature of the water in the first drain path 384. The drain line valve 341 is, under control of the control unit 112, arranged to regulate the flow in the first drain path 384 through the conductivity sensor 336. The first drain path 384 further comprises a bypass path 384*a* arranged to by-pass the conductivity sensor 336, the drain path temperature sensor 315 and the drain line valve 341. The bypass path 384*a* comprises a valve 340. The valve 340 is arranged to regulate the flow through the bypass path 384*a*.

As in FIG. 4*a*, a control device 305*a* is configured to control the flow rate of purified water in the recirculation path 375 arranged from a point downstream the heater 302, the permeate temperature sensor 303 and the additional conductivity sensor 304, and back to the tank 350. A product water pressure sensor 308 is arranged to monitor the pressure of the product water in the product water path 301*c* downstream the polisher device 306. As in FIG. 4*a*, a flow sensor 309 is arranged to monitor the flow rate of the product water downstream the polisher device 306. The pressure and the flow rate of the product water are feed to the control unit 112. The control unit 112 is configured to control the operation of the control device 305*a*. More particularly the control unit is configured to regulate the flow rate of water in the recirculation path 375 based on the pressure and flow rate of the product water, in order to control the flow rate of the product water to a desired flow rate, and the pressure of the product water to a desired pressure. The control device

305*a* is for example a motorized flow control valve that is configured to finely regulate the flow rate of water in the recirculation path 375.

A product water valve 305*d* is arranged to, under control of the control unit 112, control the produced product flow to go to either the product water port 128, or back to the tank 350 via an additional recirculation path 381. An emptying valve 396 is arranged to control the flow rate of water in the additional recirculation path 381. The additional recirculation path 381 is fluidly connected to the product water path 371*c* via an air-trap chamber 319. A product water conductivity sensor 312 is arranged to monitor the conductivity of the product water upstream the air-trap chamber 319. A product water temperature sensor 313 is configured to monitor the temperature of the product water upstream the air-trap chamber 319.

In operation, a portion of the rejected water leaving the RO-device 301 via a fluid path 385*a* passes an auxiliary constant flow device 318, which provides a steady flow of rejected water to a three-way valve 305*b* (e.g. a three-way solenoid valve) under control of control unit 112. A remaining portion of the rejected water returns to RO-pump the 450 via a valve 320 (e.g., a manual needle valve) in a first reject path 385*b*. Three-way valve 305*b* is configured to selectively divert the rejected water either to drain 339 or back to tank 350 via a second drain path 388 or back to tank 350 via a second reject path 389. A bypass-path 385*f* is arranged to bypass the auxiliary constant flow device 318. A flow control device 321 is arranged to control the flow in the bypass path 385*f* by control of the control device 112.

When a treatment is finished, the water purification apparatus 300 sets itself ready for disconnection (e.g. in response to a message received by the cycler 20) of the disposable line set 40 and closes a lid (not shown) that covers the product water port 128 and drain port 118 from the outside and at the same time connects the product water port 128 and the drain port 118 by a path 401*a*, such that heated fluid can flow from the product water port 128 and into the drain port 118 and further to the drain 339 via the first drain path 384.

All meters and sensors described in connection with water purification apparatus 300 in FIG. 6 are in some embodiments configured to send their corresponding signals to control unit 112.

In order to, as far as possible, protect the components of the water purification apparatus 300, for increased reliability, and to prevent bacterial growth, hardware and programs for cleaning are provided by the water purification apparatus 300.

The water purification apparatus 300 also comprises a container 392 containing a microbiological growth inhibiting agent. The microbiological growth inhibiting agent is used to prepare a cleaning solution such as citric acid is in some embodiments introduced into the water path. As illustrated, container 392 is in fluid communication with an inlet 392*a* of the water purification apparatus 300. In FIG. 6, the line 382 connects container 392 to the water path of the water purification apparatus 300. Alternatively, container 392 may be connected via a line (not illustrated) leading directly to disposable cassette 42 operating with cycler 20, or be connected to water line 64, or be connected to drain line 56.

The agent inhibiting microbiological growth in the container 392 may be a suitable physiologically safe acid, such as citric acid, citrate, lactic acid, acetic acid, or hydrochloric acid (or a combination thereof). In one embodiment, container 392 contains citric acid, citrate or a derivative thereof. It is noted that container 392 may also include additives provided together with the acid (such as with citric acid). A chemical inlet 392a, is located for example at the front of water purification apparatus 300. A presence sensor (not shown, e.g. an optical sensor) is arranged to sense when the container 392 is connected to the chemical inlet 392a. A three-way valve 317, under control of control unit 112, at chemical inlet 392a is arranged to open towards a second pump, being a chemical intake pump 316, and the tank 350. The chemical intake pump 316 is arranged to feed disinfecting solution into the tank 350. The optical sensor is arranged to detect if the source of cleaning or disinfection solution is connected or disconnected. If/when the container 392 is removed or is not detected by the optical sensor, the chemical intake pump 316 is stopped or not activated and three-way valve 317 is closed towards the chemical inlet 392a. Three-way valve 317, under control of control unit 112 may also be used to recirculate water and disinfectant from and to the tank 350 during the phases of chemical disinfection, cleaning and/or rinse. The chemical intake pump 316 and a valve 310 are arranged in a path 379 fluidly connecting the three-way valve 317 and the product water path 371c. The valve 310 is arranged to control the flow in the path 379.

In a more detailed disinfection phase example, when chemical disinfection is initiated, the level in the tank 350 is adjusted to a level just above low-level switch 350b. Control unit 112 causes the RO-pump 450 to start and run until empty-level switch 350a indicates a presence of air. RO-pump 450 is then stopped and inlet valve 332 is opened. Inlet valve 332 is maintained open until empty-level switch 350a indicates water. Chemical intake pump 316 is then run until a preset amount of chemical solution is inserted into the tank 350. When the level in tank 350 reaches a pre-determined level, the three-way valve 317 is opened to drain 339. RO-pump 450 circulates the water in the flow path during the chemical intake phase and may be operated in two directions to create turbulent flow and to increase disinfection time and contact. At the end of the intake phase, reject bypass valve 321 is opened and the three-way valve 305b is actuated to open the second drain path 388 to drain 339 and to drain the water level in the tank 350 to its low-level at low level switch 350b.

The described pre-treatment module 160, the RO-module 170 and post-treatment module 180, are enclosed inside of a single water purification cabinet 110a, except for the filter package 331, which is removably arranged, e.g. hinged, on the outside of the single water purification cabinet 110a. The filter package 331 may then be exchanged when exhausted. In an alternative embodiment, the modules may be arranged in separate units. As mentioned above, purified water is sent from water purification apparatus 300 to disposable set 40 via water line 64. Referring to FIG. 1, water line 64 feeds purified water to a water port 282 of cassette 42 of disposable set 40. Water line 64 is in one embodiment a flexible tube having a first end connected to the product water port 128 of the water purification apparatus 300 and a second end connected to the water port 282 of the cycler 20. Water line 64 may be at least 2 meters long and in one embodiment longer than 4 meters. Water line 64 allows water purification apparatus 300 to be installed in a room having an available water source, while cycler 20 resides in a different room in which the patient resides, e.g., sleeps. Water line 64 may accordingly be as long as necessary to connect water purification apparatus 300 to cycler 20.

FIG. 6 also illustrates that the disposable set 40 includes a drain line 56 configuration arranged to conduct water, such as used dialysis fluid, to the drain 339 of the water purification apparatus 300. Drain line 56 is e.g. a tube having a first end connected to cassette 42 of cycler 20 and a second end including a drain line connector 58 (FIG. 1) connected to a drain port 118 of the water purification apparatus 300. Drain line 56 may alternatively be a flexible tube, which may be more than 2 meters long and in some embodiments longer than 4 meters. Drain line 56 may be as long as necessary to connect between water purification apparatus 300 and cycler 20. Water line 64 and drain line 56 in the illustrated embodiment run parallel using dual lumen tubing. It is also possible that water purification apparatus 300 and cycler 20 are positioned close together, such that the same two line water path including water line 64 and drain line 56 may for example be less than 0.5 meters. Moreover, while a dual lumen water line 64 and the drain line 56 are illustrated, it is possible that water line 64 and drain line 56 are separate.

A water tray 420 is positioned below the water purification apparatus 300. A liquid sensor 370 is arranged at the bottom of the water tray 420 to detect any leakage from the water purification apparatus 300.

The present disclosure is not limited to the above-described preferred embodiments. Various alternatives, modifications and equivalents may be used. Therefore, the above embodiments should not be taken as limiting the scope of the disclosure, which is defined by the appending claims.

The invention claimed is:

1. A water purification apparatus comprising:
   a reverse osmosis device configured to produce purified water, the reverse osmosis device including a feed inlet positioned to receive feed water and a purified water outlet;
   a reverse osmosis pump configured to pump feed water to the feed inlet;
   a recirculation path configured to recirculate a proportion of the purified water from a first point downstream from the reverse osmosis device to a second point upstream of the reverse osmosis device;
   a purified water path configured to transport purified water from the purified water outlet to a destination, wherein the purified water path includes (i) a permeate water path positioned upstream of the recirculation path, and (ii) a product water path positioned downstream from the recirculation path to transport product water to the destination, wherein the permeate water path splits into the recirculation path and the product water path at the first point;
   a flow sensor configured to detect a flow rate of purified water in the permeate water path;
   a control unit configured to control the reverse osmosis pump to a certain pump rate corresponding to a certain flow rate of purified water through the permeate water path;
   a heater positioned downstream from the reverse osmosis device to heat the purified water flowing in the purified water path; and
   a temperature sensor positioned to measure a temperature of the purified water immediately downstream from the heater, wherein the control unit is configured to control the temperature of feed water flowing through a reverse osmosis membrane of the reverse osmosis device based on the temperature detected by the temperature sensor.

2. The water purification apparatus of claim 1, wherein the flow sensor is a first flow sensor, and which includes a second flow sensor configured to detect a flow rate of product water in the product water path.

3. The water purification apparatus according to claim 1, which includes at least one pressure sensor positioned and arranged to detect a pressure of purified water in the purified water path, and wherein the control unit is configured to use the detected pressure to control the pressure of the purified water so as to (i) stay below a predetermined upper pressure level or (ii) attempt to achieve a predetermined pressure.

4. The water purification apparatus according to claim 1, further comprising a tank configured to receive water from an external water source and to provide feed water to the feed inlet of the reverse osmosis device.

5. The water purification apparatus according to claim 4, wherein water from the external water source is flowed through a filter package prior to reaching the tank.

6. The water purification apparatus according to claim 4, wherein the second point upstream of the reverse osmosis device for the recirculation path is provided at the tank.

7. A water purification apparatus comprising:
   a reverse osmosis device configured to produce purified water, the reverse osmosis device including a feed inlet positioned to receive feed water and a purified water outlet;
   a reverse osmosis pump configured to pump feed water to the feed inlet;
   a recirculation path configured to recirculate a proportion of the purified water from a first point downstream from the reverse osmosis device to a second point upstream of the reverse osmosis device;
   a purified water path configured to transport purified water from the purified water outlet to a destination, wherein the purified water path includes (i) a permeate water path positioned upstream of the recirculation path, and (ii) a product water path positioned downstream from the recirculation path to transport product water to the destination, wherein the permeate water path splits into the recirculation path and the product water path at the first point;
   a flow sensor configured to detect a flow rate of purified water in the permeate water path;
   a control unit configured to control the reverse osmosis pump to a certain pump rate corresponding to a certain flow rate of purified water through the permeate water path;
   a heater positioned downstream from the reverse osmosis device to heat the purified water flowing in the purified water path;
   a temperature sensor positioned to measure a temperature of the purified water immediately downstream from the heater, wherein the control unit is configured to control the temperature of feed water flowing through a reverse osmosis membrane of the reverse osmosis device based on the temperature detected by the temperature sensor, and
   a tank configured to receive water from an external water source and to provide feed water to the feed inlet of the reverse osmosis device, wherein the tank includes an air vent line extending from an upper portion of the tank.

8. The water purification apparatus according to claim 1, further comprising a polisher device positioned downstream from the reverse osmosis device in the purified water path.

9. The water purification apparatus according to claim 1, further comprising an additional water purifier positioned downstream from the recirculation path.

10. The water purification apparatus according to claim 8, wherein the permeate water path is positioned to transport purified water from the purified water outlet of the reverse osmosis device to an inlet of the polisher device.

11. The water purification apparatus according to claim 8, wherein the product water path is positioned and arranged to transport purified water from an outlet of the polisher device to the destination.

12. The water purification apparatus according to claim 1, which includes a flow control device positioned along the recirculation path.

13. The water purification apparatus according to claim 1, wherein the destination includes a product water port.

14. The water purification apparatus according to claim 1, which includes a detector configured to detect a fluid property in the product water path, and a flow control device located along the recirculation path, wherein the control unit is configured to control the flow control device based on the fluid property detected by the detector.

15. The water purification apparatus according to claim 14, wherein the fluid property includes fluid pressure, fluid flow rate, or fluid temperature.

16. A peritoneal dialysis system comprising:
   a water purification apparatus including
      a reverse osmosis device configured to produce purified water, the reverse osmosis device including a feed inlet positioned to receive feed water and a purified water outlet,
      a reverse osmosis pump configured to pump feed water to the feed inlet,
      a recirculation path configured to recirculate a proportion of the purified water from a first point downstream from the reverse osmosis device to a second point upstream of the reverse osmosis device,
      a purified water path configured to transport purified water from the purified water outlet to a destination, wherein the purified water path includes (i) a permeate water path positioned upstream of the recirculation path, and (ii) a product water path positioned downstream from the recirculation path to transport product water to the destination, wherein the permeate water path splits into the recirculation path and the product water path at the first point,
      a flow sensor configured to detect a flow rate of purified water in the permeate water path, and
      a control unit configured to control the reverse osmosis pump to a certain pump rate corresponding to a certain flow rate of purified water through the permeate water path,
      a heater positioned downstream from the reverse osmosis device to heat the purified water flowing in the purified water path,
      a temperature sensor positioned to measure a temperature of the purified water immediately downstream from the heater, wherein the control unit is configured to control the temperature of feed water flowing through a reverse osmosis membrane of the reverse osmosis device based on the temperature detected by the temperature sensor, and
   a peritoneal dialysis ("PD") cycler positioned and arranged to use PD fluid during a PD treatment, the PD fluid mixed using product water from the water purification apparatus.

17. The water purification apparatus according to claim 16, wherein the destination includes a product water port.

18. A method for controlling at least one fluid property in a water purification apparatus, the water purification apparatus including a reverse osmosis device configured to produce purified water, a reverse osmosis pump configured to pump feed water, and a recirculation path arranged to recirculate a proportion of the purified water from a first point downstream from the reverse osmosis device to a second point upstream of the reverse osmosis device, the method comprising:

arranging a purified water path to include (i) a permeate water path positioned upstream of the recirculation path and (ii) a product water path positioned downstream from the recirculation path;

splitting the permeate water path into the recirculation path and the product water path at the first point;

controlling the reverse osmosis pump to a certain pump rate corresponding to a certain flow rate of purified water through the permeate water path;

monitoring a temperature sensor positioned immediately downstream of a heater to detect a temperature of the purified water; and controlling the temperature of water flowing through a reverse osmosis membrane of the reverse osmosis device based on the temperature detected by the temperature sensor.

19. The method according to claim 18, further comprising estimating an amount of product water produced during a production time period based on a duration of the production time period and a corresponding flow rate of the purified water detected during the production time period.

20. The method according to claim 19, further comprising triggering a predetermined action when the amount reaches a pre-defined production volume.

21. The method according to claim 18, which includes monitoring at least one pressure sensor positioned and arranged to detect a pressure of purified water in the purified water path, and using the detected pressure to control the pressure of the purified water so as to (i) stay below a predetermined upper pressure level or (ii) attempt to achieve a predetermined pressure.

\* \* \* \* \*